US010593036B2

(12) United States Patent
Kinukawa et al.

(10) Patent No.: US 10,593,036 B2
(45) Date of Patent: Mar. 17, 2020

(54) SPERM INSPECTION METHOD AND DEVICE

(71) Applicant: Livestock Improvement Association of Japan, Inc., Tokyo (JP)

(72) Inventors: Masashi Kinukawa, Tokyo (JP); Kyoko Uchiyama, Tokyo (JP)

(73) Assignee: Livestock Improvement Association of Japan, Inc., Tokyo (JP)

( * ) Notice: Subject to any disclaimer, the term of this patent is extended or adjusted under 35 U.S.C. 154(b) by 124 days.

(21) Appl. No.: 15/124,998

(22) PCT Filed: Mar. 12, 2015

(86) PCT No.: PCT/JP2015/057380
§ 371 (c)(1),
(2) Date: Sep. 9, 2016

(87) PCT Pub. No.: WO2015/137466
PCT Pub. Date: Sep. 17, 2015

(65) Prior Publication Data
US 2017/0091926 A1     Mar. 30, 2017

(30) Foreign Application Priority Data
Mar. 12, 2014    (JP) ................. 2014-049033

(51) Int. Cl.
*G06T 7/00*      (2017.01)
*G01N 33/68*      (2006.01)

(52) U.S. Cl.
CPC ......... *G06T 7/0012* (2013.01); *G01N 33/689* (2013.01); *G06T 2207/10004* (2013.01)

(58) Field of Classification Search
CPC ............... G01N 21/00; G01N 33/4833; G01N 33/48735; G06T 7/0012
USPC ......................................................... 702/19
See application file for complete search history.

(56) References Cited

FOREIGN PATENT DOCUMENTS

| JP | 2002-500866 A | 1/2002 |
|---|---|---|
| JP | 2005-74586 A | 3/2005 |
| JP | 2009-288189 A | 12/2009 |
| WO | 99/37147 A1 | 7/1999 |
| WO | 2012/061578 A2 | 5/2012 |

OTHER PUBLICATIONS

Ramón et al., "Sperm Population Structure and Male Fertility: An Intraspecific Study of Sperm Design and Velocity in Red Deer", Biology of Reproduction, 89(5):110, 1-7 (2013).
Maree et al., "Quantification and identification of sperm subpopulations using computer-aided sperm analysis and species-specific cut-off values for swimming speed", Biotechnic and Histochemistry, 88(3-4):181-193 (2013).
Shibahara et al., "Prediction of Human Sperm Fertilizing Ability by the Hyperactivated Motility Patterns," Journal of Mammalian Ova Research, 20:29-33 (2003).
Smith et al., "Liner Collection Cone and pH Effects on Postthaw Motility, Staining, and Acrosomes of Bovine Spermatozoa," J Dairy Sci, 74(4):1310-1313 (1991).
Ijaz et al., "Effect of Washing and Capacitating Media pH on Bull Sperm Motility, Acroemme Integrity, and Ability of Penetrate Zona-Free Hamster Oocytes," J Dairy Sci, 72:2691-2699 (1989).
Rrodiríguez-Martínez, "Can We Increase the Estimative Value of Semen Assessment?" Reprod. Domest. Anim., 41(Suppl. 2):2-10 (2006).
Hamano et al, "Evaluation on the Fertility of Japanese Black Bull with Motility, Hypoosmotic Solution and Cervical Mucus test," Journal of the Hokuriku Branch of the Japan Society of Animal Science, 81:63-68 (2000).
Suarez, "Regulation of sperm storage and movement in the mammalian oviduct," International Journal of Developmental Biology, 52:455-462 (2008).
International Search Report for PCT/JP2015/057380 (dated Jun. 2, 2015).
Office Action for Japanese Patent Application No. 2016-507833, dated Dec. 18, 2018.

*Primary Examiner* — Jerry Lin
(74) *Attorney, Agent, or Firm* — Merchant & Gould P.C.

(57) ABSTRACT

The present invention addresses the problem of developing a simple sperm inspection method and device for reflecting fertility. In the present invention, a simple sperm inspection method and device having a high correlation with fertility can be provided by suspending a sperm population in an inspection liquid and measuring a quality indicator value for each sperm, stratifying the sperm population on the basis of the sperm quality indicator value, and evaluating the quality of the sperm on the basis of the quality indicator value of one or a plurality of groups in the stratified population. This standard can predict fertility with higher precision through use of a graph in which the quality indicator values for individual sperm of the sperm population are arranged in sequence. Sperm motility is preferably used as a sperm quality indicator.

16 Claims, 19 Drawing Sheets

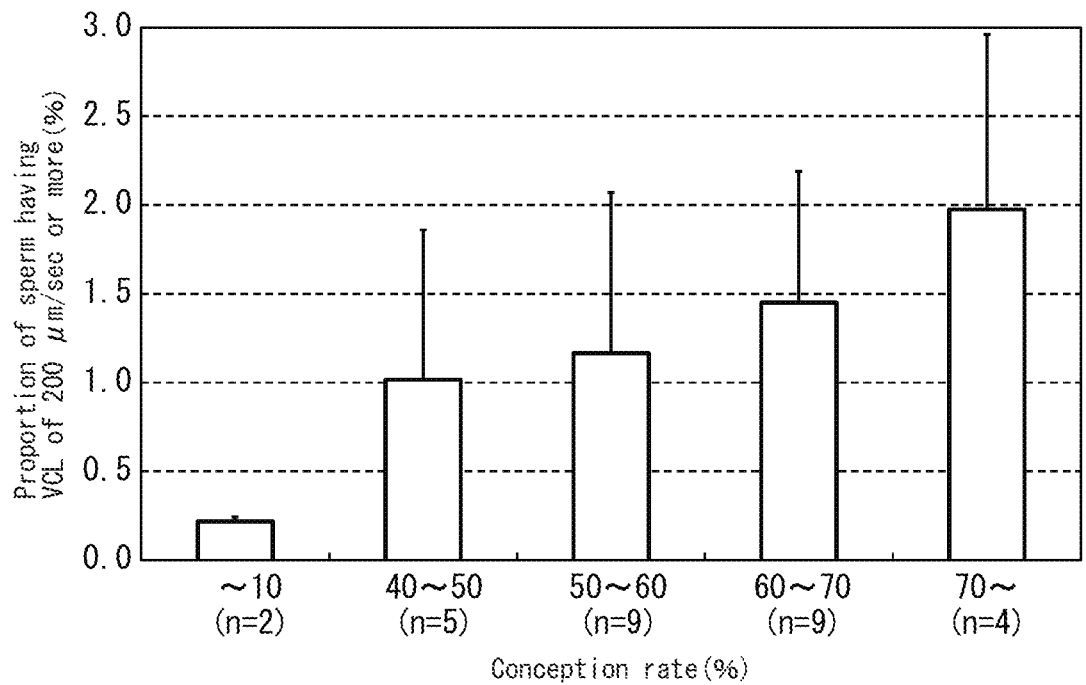
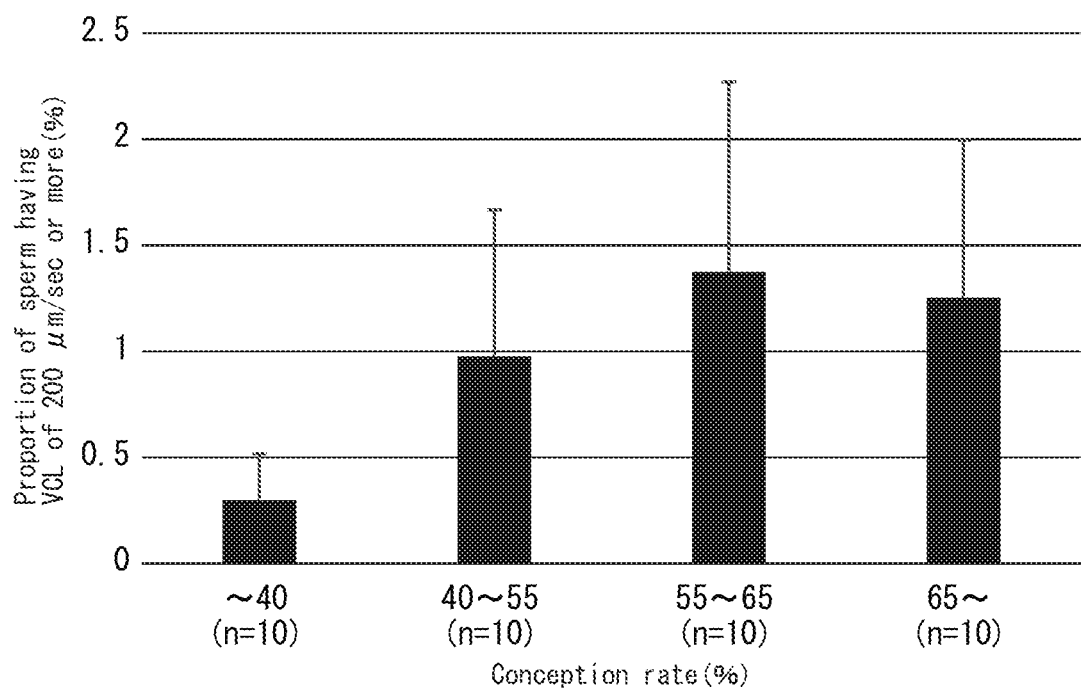

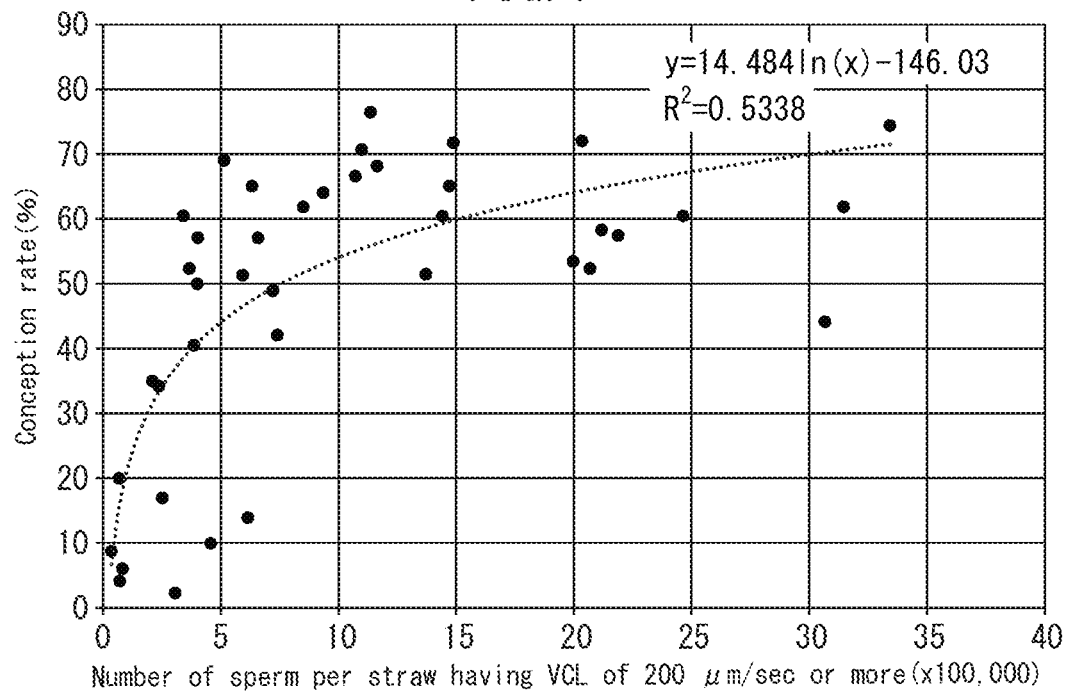
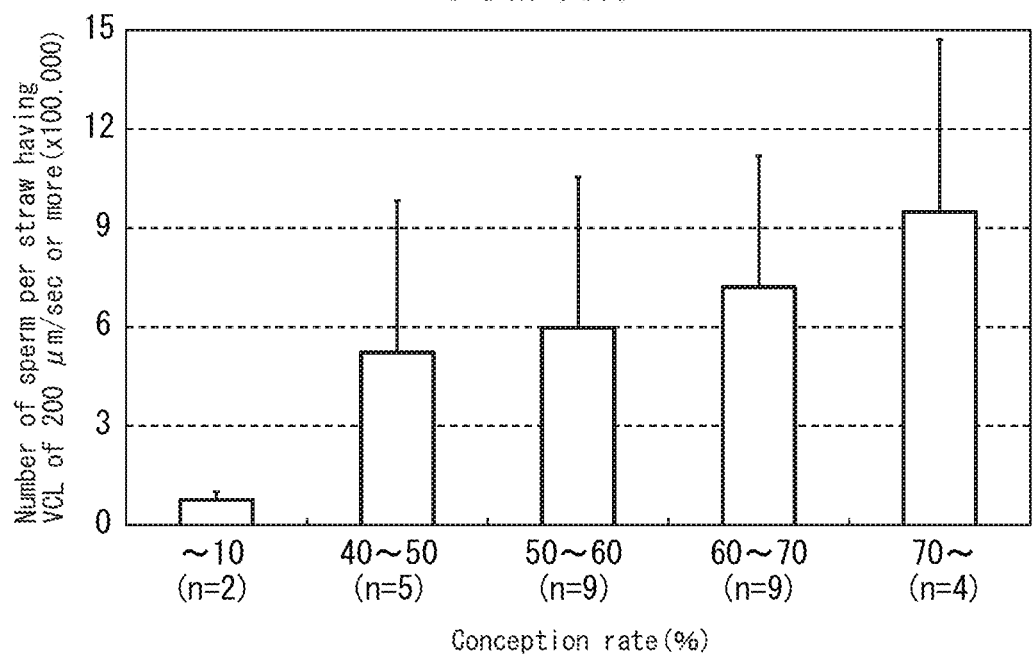

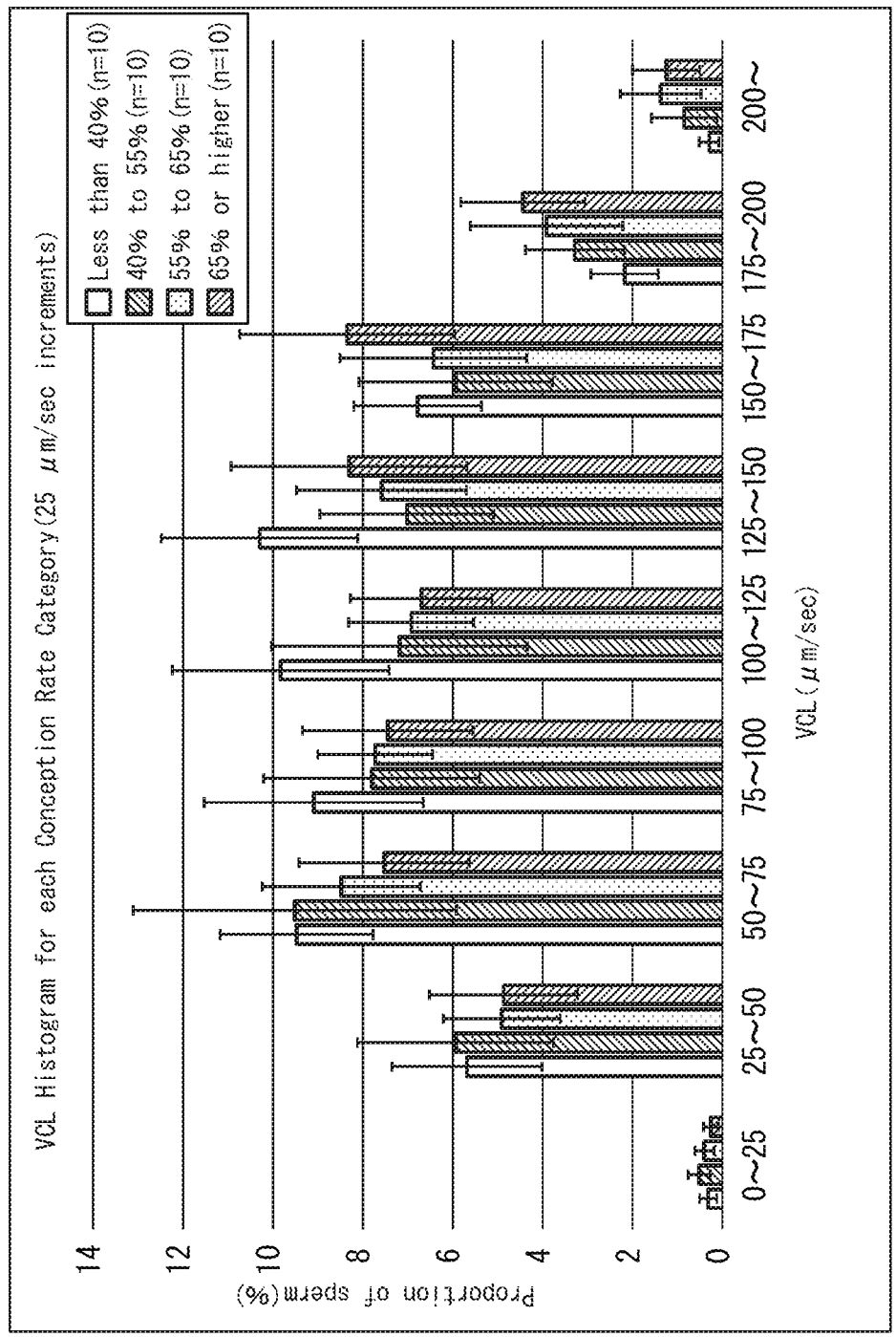

SPERM INSPECTION METHOD AND DEVICE

This application is a U.S. National Stage Application under 35 U.S.C. §371 of International Patent Application No. PCT/JP2015/057380 filed Mar. 12, 2015, which claims the benefit of priority to Japanese Patent Application No. 2014-049033 filed Mar. 12, 2014, the disclosures of all of which are hereby incorporated by reference in their entireties. The International Application was published in Japanese on Sept. 17, 2015 as WO 2015/137466.

TECHNICAL FIELD

The present invention relates to a sperm inspection method and device capable of predicting fertility, a control program that allows an information processing device to determine sperm quality, and a computer-readable medium that encodes the control program.

BACKGROUND

Being able to predict conception chance by a simple method for the sperm of all animals would be extremely useful in terms of both cost and labor. In the case of livestock, for example, since it is necessary to obtain offspring through efficient conception, it is important to provide semen for which fertility is guaranteed. From this viewpoint, there is a desire to develop a method for evaluating the quality of sperm that accurately reflects fertility.

With respect to cattle breeding, for example, although the proliferation of artificial insemination in Japan is nearly 100%, the resulting conception rate is decreasing each year. Among dairy breeds, although the conception rate after first insemination was 62.4% and the conception rate after 1 to 3 inseminations was 62.0% in 1989, the conception rate after first insemination had decreased to 45.6% and the conception rate after 1 to 3 inseminations had decreased to 44.4% in 2011, (Non-Patent Document 1: Livestock Improvement Association of Japan, Inc., 2011 Conception Survey Results (2013)). Under the present circumstances in which conception rate is exhibiting a decreasing trend in this manner, the providing of semen for which fertility is guaranteed would be extremely useful from the viewpoint of production efficiency.

Conventionally, inspection of sperm quality has focused primarily on such factors as sperm viability, sperm motility rate, sperm motility retention rate, mitochondria normal rate, acrosome normal rate or sperm morphology normal rate (Patent Document 1: Japanese Patent No. 5092149, Non-Patent Document 2: Rodriguez-Martinez H., Reprod. Domest. Anim. 41, Suppl. 2, 2-10 (2006)). However, the correlations between these inspection methods and conception chance have not necessarily been high for all parameters, thereby preventing these inspection methods from serving as simple indicators reflective of fertility relative to sperm. The cause of the lack of a high correlation between these inspection methods and fertility is thought to be because these methods do not reflect sperm behavior in the female body or the environment at the time of fertilization.

Once sperm has reached the ampulla of the fallopian tube, motility increases prominently when the female ovulates, and sperm that exhibits hyperactivated motility is thought to result in successful conception (Non-Patent Document 3: Suarez, S. S., Int. J. Dev. Biol. 52 (5-6), 455-62 (2008)). Therefore, an inspection method has been proposed that reflects actual conditions inside the female body (Non-Patent Document 4: Hamano, et al, Journal of the Hokuriku Branch of the Japan Society of Animal Science 81, 63-68 (2000)). In addition, inspections can also be carried out using an in vitro fertilization test in which sperm is actually made to fertilize an egg.

PRIOR ART DOCUMENTS

Patent Documents

Patent Document 1: Japanese Patent No. 5092149

Non-Patent Documents

Non-Patent Document 1: Livestock Improvement Association of Japan, Inc., 2011 Conception Survey Results (2013)
Non-Patent Document 2: Rodriguez-Martinez H., Reprod. Domest. Anim. 41, Suppl. 2, 2-10 (2006)
Non-Patent Document 3: Suarez, S. S., Int. J. Dev. Biol. 52 (5-6), 455-62 (2008)
Non-Patent Document 4: Hamano, et al, Journal of the Hokuriku Branch of the Japan Society of Animal Science 81, 63-68 (2000)
Non-Patent Document 5: Kinukawa, M., Doctorate Thesis, http://hdl.handle.net/2261/119 (2005)
Non-Patent Document 6: Guthrie, et al, Biology of Reproduction 67, 1811-1816 (2002)

DISCLOSURE OF THE INVENTION

Problems to be Solved by the Invention

However, since the method described in Non-Patent Document 4 and in vitro fertilization testing require considerable costs and labor, it is difficult to perform inspections on all semen desired to be provided easily and at low cost. In addition, these inspections cannot be said to completely mimic the environment within the female body with high reliability. Therefore, there is a desire to develop a simple sperm inspection method and device that easily reproduces the fertilization environment within the female body in vitro and reflects the fertility of the sperm.

With the foregoing in view, an object of the present invention is to provide a sperm inspection method and device that solves the aforementioned problems.

Means for Solving the Problems

As a result of conducting extensive studies on sperm quality inspections using semen having a known conception chance to solve the aforementioned problems, the quality of sperm having a high correlation with fertility was able to be evaluated by assessing the proportion and number of sperm having an extremely high value for a sperm quality indicator. Moreover, the quality of sperm having a high correlation with fertility was able to be easily evaluated by stratifying a sperm population based on a quality evaluation value of the sperm, and evaluating sperm quality based on the quality evaluation value of one or a plurality of groups of the stratified population. As a result, the present invention relates to a sperm inspection method, sperm inspection device, control program for allowing an information processing device to determine sperm quality, and a recording medium that encodes the control program.

Thus, the present invention employs the configurations listed below.

The sperm inspection method of the present invention is characterized in that it is provided with a step for suspending a sperm population in an inspection liquid and measuring a quality indicator value of each sperm, and a step for evaluating sperm quality based on the quality indicator value.

In addition, the step for evaluating sperm quality is characterized by stratifying the sperm population based on a quality indicator value, and evaluating based on the quality indicator value of one or a plurality of groups of the stratified population.

In addition, the quality indicator value of a stratified population is characterized by the mean, median or mode of the quality indicator value for each population.

In addition, the stratification is characterized by selecting a high quality group based on a quality indicator value.

In addition, the stratification is characterized by evaluating sperm quality based on the quality indicator value of still another group.

In addition, the high quality group is characterized by lying within the upper 50%.

In addition, the high quality group is characterized by lying within the upper 20%.

In addition, the high quality group is characterized by lying within the upper 10%.

In addition, the high quality group is characterized by lying within the upper 5%.

In addition, the high quality group is characterized by lying within the upper 3%.

In addition, the high quality group is characterized by lying within the upper 1%.

In addition, the high quality group is characterized by lying within the upper 0.5%.

In addition, the high quality group is characterized by lying within the upper 0.3%.

In addition, the quality indicator value of the high quality group is characterized by the mean, median or mode of the quality indicator value in the high quality group.

In addition, the sperm population is characterized by being viable sperm.

In addition, the sperm population is characterized in that, sperm motility is of a certain value or higher or within a certain range.

In addition, quality indictor is characterized by being an indicator of sperm motility.

In addition, the inspection liquid is characterized in that the pH is 6.0 to 9.0.

In addition, the inspection liquid is characterized in that the pH is 7.2 to 8.2

In addition, the inspection liquid is characterized in that the pH is 7.4 to 7.8.

In addition, the inspection liquid is characterized in that the osmotic pressure is 230 to 400 mmol/kg (mOsm/kg).

In addition, the inspection liquid is characterized by being maintained at 33 to 43° C.

In addition, the inspection liquid is characterized by being maintained at 36 to 40° C.

In addition, the inspection liquid is characterized by containing a buffer, a sugar and a salt.

In addition, the buffer of the inspection liquid is characterized by consisting of tris(hydroxymethyl)aminomethane and citric acid.

In addition, the sugar of the inspection liquid is characterized by being glucose.

In addition, the salt of the inspection liquid is characterized by being sodium chloride.

In addition, the inspection liquid is characterized by containing an activator.

In addition, the activator is characterized by being procaine, caffeine and/or theophylline.

In addition, the inspection liquid is characterized by containing a loading agent.

In addition, the loading agent is characterized by being polyvinyl pyrrolidone K-90.

In addition, the duration of suspension is characterized by being from immediately after suspending to 30 minutes after suspending.

In addition, the indicator of sperm motility is characterized by being VAP, VCL, ALH and/or BCF.

In addition, the step for evaluating sperm quality is characterized by containing a step for determining sperm quality by comparing with a quality indicator reference value of one or a plurality of groups.

In addition, the quality indictor reference value is characterized in that VCL is 150 μm/sec or more.

In addition, the quality indicator reference value is characterized in that VCL is 200 μm/sec or more.

In addition, the step for evaluating sperm quality is characterized by being based on the proportion or number of sperm that exceeds a prescribed quality indicator reference value.

In addition, the prescribed quality indicator reference value is characterized by being a value selected from the group consisting of VCL values of 150 μm/sec, 175 μm/sec and 200 μm/sec.

In addition, the prescribed quality indicator reference value is characterized in that VCL is 200 μm/sec or more.

In addition, the proportion of sperm is characterized by being 1% or more.

In addition, the proportion of sperm is characterized by being 0.7% or more

In addition, the proportion of sperm is characterized by being 0.3% or more.

In addition, the number of sperm is characterized by being 300,000 sperm or more per straw.

In addition, the number of sperm is characterized by being 100,000 sperm or more per straw.

In addition, the step for evaluating sperm quality is characterized by determining the quality indicator values of individual sperm of the sperm population from a graph in which they are sequentially arranged.

In addition, the step for evaluating sperm quality is characterized by determining the quality indicator values of individual sperm of the sperm population from an approximation line of the graph in which they are sequentially arranged.

In addition, the step for evaluating sperm quality is characterized by determining the quality indicator values of individual sperm of the sperm population from the slope of an approximation line of the graph in which they are sequentially arranged.

In addition, the step for evaluating sperm quality is characterized by determining the quality indicator values of individual sperm of the sperm population from a coefficient of an approximation line of the graph in which they are sequentially arranged.

In addition, the step for evaluating sperm quality is characterized by determining the quality indicator values of individual sperm of the sperm population from an intercept of an approximation line of the graph in which they are sequentially arranged.

In addition, the sperm is characterized by being mammalian sperm.

In addition, the sperm is characterized by being bovine sperm.

A sperm inspection device of the present invention is characterized by being provided with a sperm quality measurement means that measures a quality indicator value of individual sperm of a sperm population suspended in an inspection liquid, and a sperm quality evaluation means that evaluates sperm quality based on the quality indicator value.

In addition, the sperm quality evaluation means is characterized by stratifying the sperm population based on a quality indicator value, and evaluating based on the quality indicator value of one or a plurality of groups of the stratified population.

In addition, the quality indicator value of a stratified population is characterized by the mean, median or mode of the quality indicator values for each population.

In addition, the stratification is characterized by selecting a high quality group based on a quality indicator value.

In addition, the stratification is characterized by evaluating sperm quality based on the quality indicator of still another group.

In addition, the high quality group is characterized by lying within the upper 50%.

In addition, the high quality group is characterized by lying within the upper 20%.

In addition, the high quality group is characterized by lying within the upper 10%.

In addition, the high quality group is characterized by lying within the upper 5%.

In addition, the high quality group is characterized by lying within the upper 3%.

In addition, the high quality group is characterized by lying within the upper 1%.

In addition, the high quality group is characterized by lying within the upper 0.5%.

In addition, the high quality group is characterized by lying within the upper 0.3%.

In addition, the quality indicator value of the high quality group is characterized by the mean, median or mode of the quality indicator value in the high quality group.

In addition, the sperm population is characterized by being viable sperm.

In addition, the sperm population is characterized in that sperm motility is of a certain value or higher or within a certain range.

In addition, quality indictor is characterized by being an indicator of sperm motility.

In addition, the inspection liquid is characterized in that the pH is 6.0 to 9.0.

In addition, the inspection liquid is characterized in that the pH is 7.2 to 8.2 In addition, the inspection liquid is characterized in that the pH is 7.4 to 7.8.

In addition, the inspection liquid is characterized in that the osmotic pressure 230 to 400 mmol/kg (mOsm/kg).

In addition, the inspection liquid is characterized by being maintained at 33 to 43° C.

In addition, the inspection liquid is characterized by being maintained at 36 to 40° C.

In addition, the inspection liquid is characterized by containing a buffer, a sugar and a salt.

In addition, the buffer of the inspection liquid is characterized by consisting of tris(hydroxymethyl)aminomethane and citric acid.

In addition, the sugar of the inspection liquid is characterized by being glucose.

In addition, the salt of the inspection liquid is characterized by being sodium chloride.

In addition, the inspection liquid is characterized by containing an activator.

In addition, the activator is characterized by being procaine, caffeine and/or theophylline.

In addition, the inspection liquid is characterized by containing a loading agent.

In addition, the loading agent is characterized by being polyvinyl pyrrolidone K-90.

In addition, the duration of suspension is characterized by being from immediately after suspending to 30 minutes.

In addition, the indicator of sperm motility is characterized by being VAP, VCL, ALH and/or BCF.

In addition, the sperm quality evaluation means is characterized by containing a means for determining sperm quality by comparing with a quality indicator reference value of one or a plurality of groups.

In addition, the quality indictor reference value is characterized in that VCL is 150 µm/sec or more.

In addition, the quality indicator reference value is characterized in that VCL is 200 µm/sec or more.

In addition, the sperm quality evaluation means is characterized by being based on the proportion or number of sperm that exceeds a prescribed quality indicator reference value.

In addition, the prescribed quality indicator reference value is characterized by being a value selected from the group consisting of VCL values of 150 µm/sec, 175 µm/sec and 200 µm/sec.

In addition, the prescribed quality indicator reference value is characterized in that VCL is 200 µm/sec or more.

In addition, the proportion of sperm is characterized by being 1% or more.

In addition, the proportion of sperm is characterized by being 0.3% or more.

In addition, the number of sperm is characterized by being 300,000 sperm or more per straw.

In addition, the number of sperm is characterized by being 100,000 sperm or more per straw.

In addition, the sperm quality evaluation means is characterized by determining the quality indicator values of individual sperm of the sperm population from a graph in which they are sequentially arranged.

In addition, the sperm quality evaluation means is characterized by determining the quality indicator values of individual sperm of the sperm population from an approximation line of the graph in which they are sequentially arranged.

In addition, the sperm quality evaluation means is characterized by determining the quality indicator values of individual sperm of the sperm population from the slope of an approximation line of the graph in which they are sequentially arranged.

In addition, the sperm quality evaluation means is characterized by determining the quality indicator values of individual sperm of the sperm population from a coefficient of an approximation line of the graph in which they are sequentially arranged.

In addition, the step for evaluating sperm quality is characterized by determining the quality indicator values of individual sperm of the sperm population from an intercept of an approximation line of the graph in which they are sequentially arranged.

In addition, the sperm is characterized by being mammalian sperm.

In addition, the sperm is characterized by being bovine sperm.

The control program of the present invention is characterized by being a control program that allows an information processing device containing an output unit and a storage unit to determine sperm quality, wherein storage of a quality indicator value of individual sperm in a sperm population in an inspection liquid in the storage unit, stratification of the sperm population based on the stored quality indicator value, determination of sperm quality based on the quality indicator value of the stratified population, and output of the sperm quality results to the output unit are made to be executed by the information processing device.

In addition, the information processing device is characterized in that it further has an image capturing unit, wherein the image capturing unit acquires a plurality of images over time, and a quality indicator is determined based on a plurality of images.

In addition, determination of sperm quality based on the quality indicator value of one or a plurality of groups of the stratified population contains the following:

calculation of a quality determination value from the quality indicator value of the stratified population, and determining sperm quality based on the quality determination value.

In addition, the quality indicator value of a stratified population is characterized by the mean, median or mode of the quality indicator value for each population.

In addition, the stratification is characterized by selecting a high quality group for the stratified population.

In addition, the stratification is characterized by evaluating sperm quality based on the quality indicator value of still another group.

In addition, the high quality group is characterized by lying within the upper 50%.

In addition, the high quality group is characterized by lying within the upper 20%.

In addition, the high quality group is characterized by lying within the upper 10%.

In addition, the high quality group is characterized by lying within the upper 5%.

In addition, the high quality group is characterized by lying within the upper 3%.

In addition, the high quality group is characterized by lying within the upper 1%.

In addition, the high quality group is characterized by lying within the upper 0.5%.

In addition, the high quality group is characterized by lying within the upper 0.3%.

In addition, the quality indicator value of the high quality group is characterized by the mean, median or mode of the quality indicator value in the high quality group.

In addition, the sperm population is characterized by being viable sperm.

In addition, the sperm population is characterized in that sperm motility is of a certain value or higher or within a certain range.

In addition, quality indictor is characterized by being an indicator of sperm motility.

In addition, the inspection liquid is characterized in that the pH is 6.0 to 9.0.

In addition, the inspection liquid is characterized in that the pH is 7.2 to 8.2

In addition, the inspection liquid is characterized in that the pH is 7.4 to 7.8.

In addition, the inspection liquid is characterized in that the osmotic pressure 230 to 400 mmol/kg (mOsm/kg).

In addition, the inspection liquid is characterized by being maintained at 33 to 43° C.

In addition, the inspection liquid is characterized by being maintained at 36 to 40° C.

In addition, the inspection liquid is characterized by containing a buffer, a sugar and a salt.

In addition, the buffer of the inspection liquid is characterized by consisting of tris(hydroxymethyl)aminomethane and citric acid.

In addition, the sugar of the inspection liquid is characterized by being glucose.

In addition, the salt of the inspection liquid is characterized by being sodium chloride.

In addition, the inspection liquid is characterized by containing an activator.

In addition, the activator is characterized by being procaine, caffeine and/or theophylline.

In addition, the inspection liquid is characterized by containing a loading agent.

In addition, the loading agent is characterized by being polyvinyl pyrrolidone K-90.

In addition, the duration of suspension is characterized by being from immediately after suspending to 30 minutes.

In addition, the indicator of sperm motility is characterized by being VAP, VCL, ALH and/or BCF.

In addition, the evaluation of sperm quality is characterized by including determination of sperm quality by comparing with a quality indicator reference value of one or a plurality of groups.

In addition, the quality indictor reference value is characterized in that VCL is 150 μm/sec or more.

In addition, the quality indicator reference value is characterized in that VCL is 200 μm/sec or more.

In addition, the evaluation of sperm quality is characterized by being based on the proportion or number of sperm that exceeds a prescribed quality indicator reference value.

In addition, the prescribed quality indicator reference value is characterized by being a value selected from the group consisting of VCL values of 150 μm/sec, 175 μm/sec and 200 μm/sec.

In addition, the prescribed quality indicator reference value is characterized in that VCL is 200 μm/sec or more.

In addition, the proportion of sperm is characterized by being 1% or more.

In addition, the proportion of sperm is characterized by being 0.3% or more.

In addition, the number of sperm is characterized by being 300,000 sperm or more per straw.

In addition, the number of sperm is characterized by being 100,000 sperm or more per straw.

In addition, the evaluation of sperm quality is characterized by determining the quality indicator values of individual sperm of the sperm population from a graph in which they are sequentially arranged.

In addition, the evaluation of sperm quality is characterized by determining the quality indicator values of individual sperm of the sperm population from an approximation line of the graph in which they are sequentially arranged.

In addition, the evaluation of sperm quality is characterized by determining the quality indicator values of individual sperm of the sperm population from the slope of an approximation line of the graph in which they are sequentially arranged.

In addition, the evaluation of sperm quality is characterized by determining the quality indicator values of individual sperm of the sperm population from a coefficient of an approximation line of the graph in which they are sequentially arranged.

In addition, the evaluation of sperm quality is characterized by determining the quality indicator values of individual sperm of the sperm population from an intercept of an approximation line of the graph in which they are sequentially arranged.

In addition, the sperm is characterized by being mammalian sperm.

In addition, the sperm is characterized by being bovine sperm.

Effects of the Invention

According to the present invention, a method for easily inspecting sperm can be provided that demonstrates a high correlation with fertility according to a quality determination value based on a quality indicator value of a high quality group. According to the inspection method of the present invention, since fertility can be easily predicted, sperm having a high fertility can be efficiently provided by preliminarily investigating the semen used. In addition, since an accurate indicator of sperm quality can be provided in the development of diluents for refrigerated or frozen storage, development is able to proceed more efficiently.

BRIEF DESCRIPTION OF THE DRAWINGS

FIG. 8A is a graph comparing the proportion of sperm having VCL of 200 μm/sec or more for each category of conception rate as determined by measuring 3 lots each of sperm of 29 bulls having known conception rates. Values are indicated as the mean and standard deviation. Samples having a high conception rate were able to be confirmed to have a high proportion of sperm having VCL of 200 μm/sec or more.

FIG. 8B is a graph comparing the proportion of sperm having VCL of 200 μm/sec or more for each category of conception rate as determined by measuring 3 lots each of sperm of 40 bulls having known conception rates. Values are indicated as the mean and standard deviation.

Samples having a high conception rate were able to be confirmed to have a high proportion of sperm having VCL of 200 μm/sec or more.

FIG. 9 is graph showing the correlation between the number of sperm in a single straw having VCL of 200 μm/sec or more and conception rate as determined by measuring 3 lots each of sperm of 40 bulls having known conception rates. A high correlation (r=0.7306, p<0.001) was able to be confirmed between the number of sperm in a single straw having VCL of 200 μm/sec or more and conception rate.

FIG. 10A is a graph comparing the number of sperm per single straw having VCL of 200 μm/sec or more for each category of conception rate as determined by measuring 3 lots each of sperm of 29 bulls having known conception rates. Values are indicated as the mean and standard deviation. Samples having a high conception rate were able to be confirmed to have a high proportion of sperm having VCL of 200 μm/sec or more in a single straw.

Figure 10B:
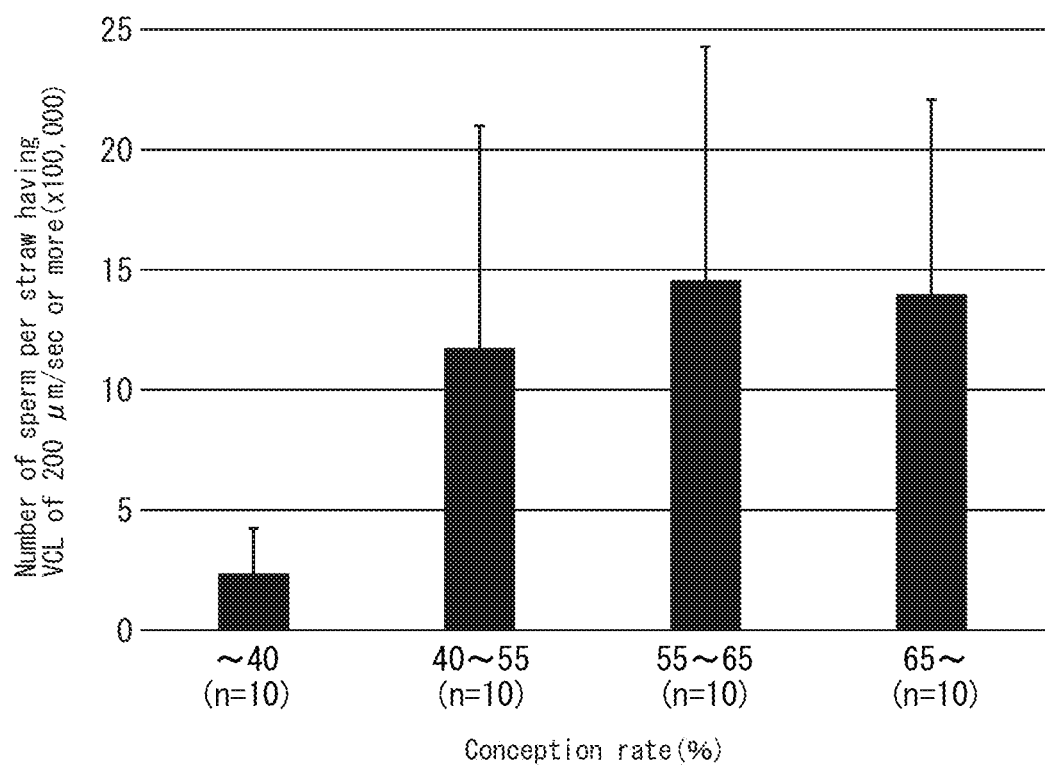

FIG. 10B is a graph comparing the number of sperm per single straw having VCL of 200 μm/sec or more for each category of conception rate as determined by measuring 3 lots each of sperm of 40 bulls having known conception rates. Values are indicated as the mean and standard deviation. Samples having a high conception rate were able to be confirmed to have a high proportion of sperm having VCL of 200 μm/sec or more in a single straw.

Figure 11A:
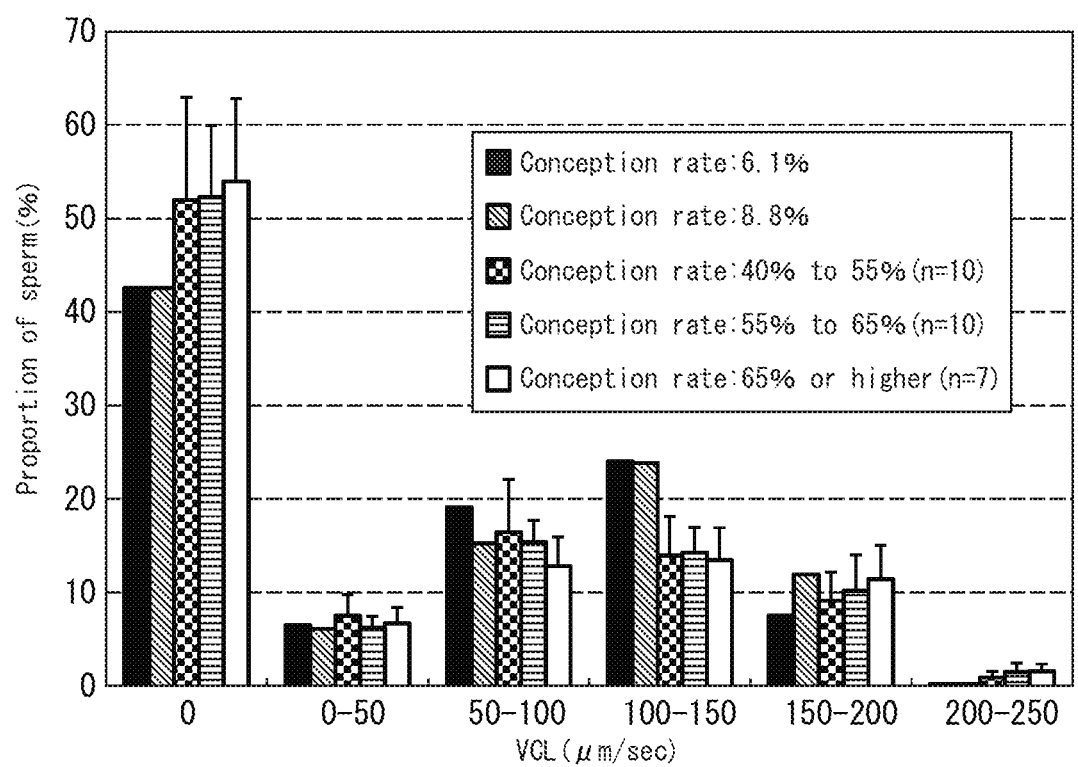

FIG. 11A is a graph showing the proportions of sperm for each group by dividing into six groups based on VCL value determined by measuring 3 lots each of sperm of 29 bulls having known conception rates. Values are indicated as mean values. Samples having a low conception rate exhibited a low proportion of sperm having VCL of 200 μm/sec or more and a large proportion of sperm having VCL of 100 to 150 μm/sec.

FIG. 11B is a graph showing the proportions of sperm for each group by dividing into nine groups based on VCL value determined by measuring 3 lots each of sperm of 40 bulls having known conception rates. Values are indicated as means values. The proportion of sperm having VCL of 175 μm/sec or more decreased as fertility became lower. In the case of samples having a conception rate of less than 40%, the proportion of sperm having VCL of 75 to 150 μm/sec was high. In the case of samples having a conception rate of less than 40% or 40 to 55%, the proportion of sperm having VCL of 25 to 75 μm/sec was high.

Figure 12A:
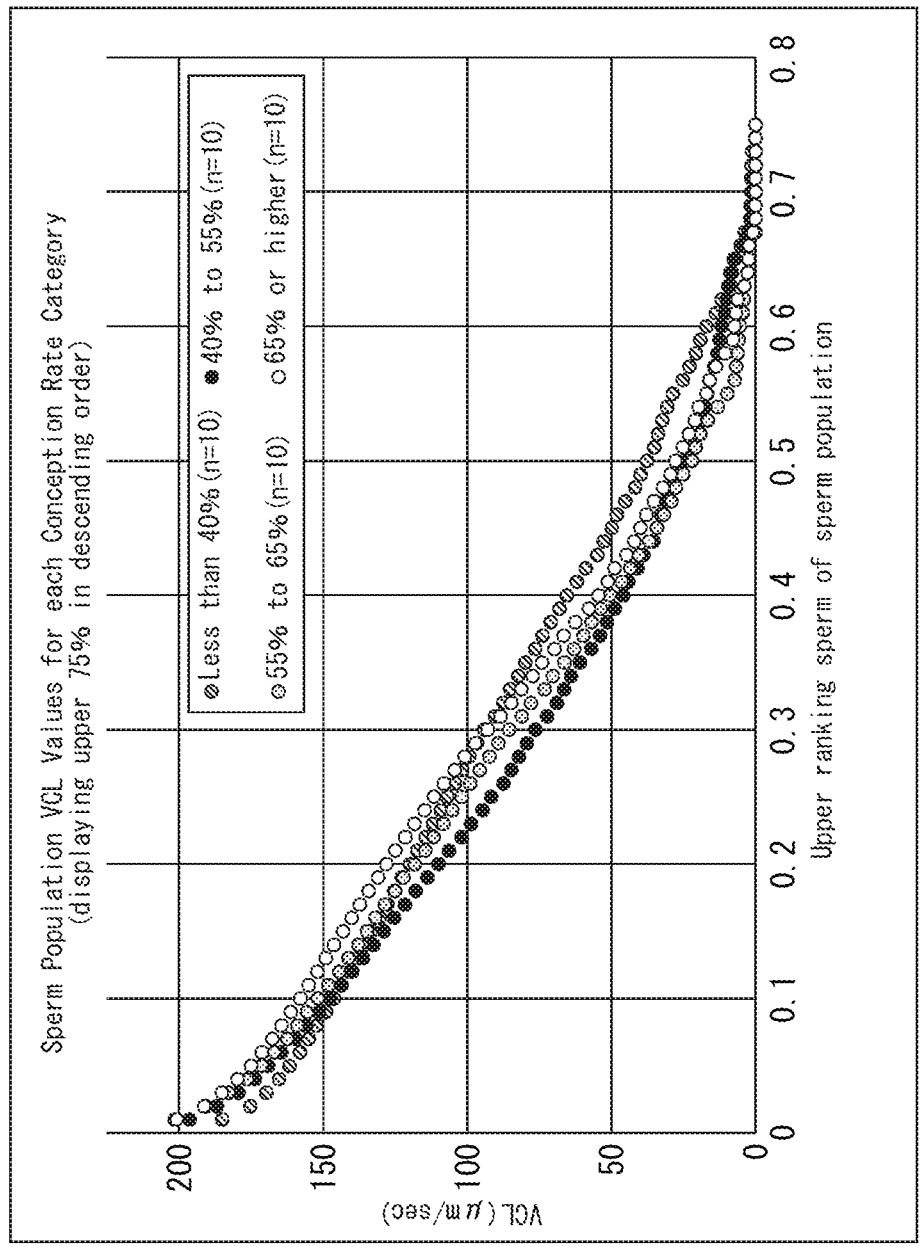

FIG. 12A is graph showing the VCL values of sperm in the upper 75% for each category of conception rate arranged in descending order as determined by measuring 3 lots each of sperm of 40 bulls having known conception rates. Values are indicated as mean values.

Figure 12B:
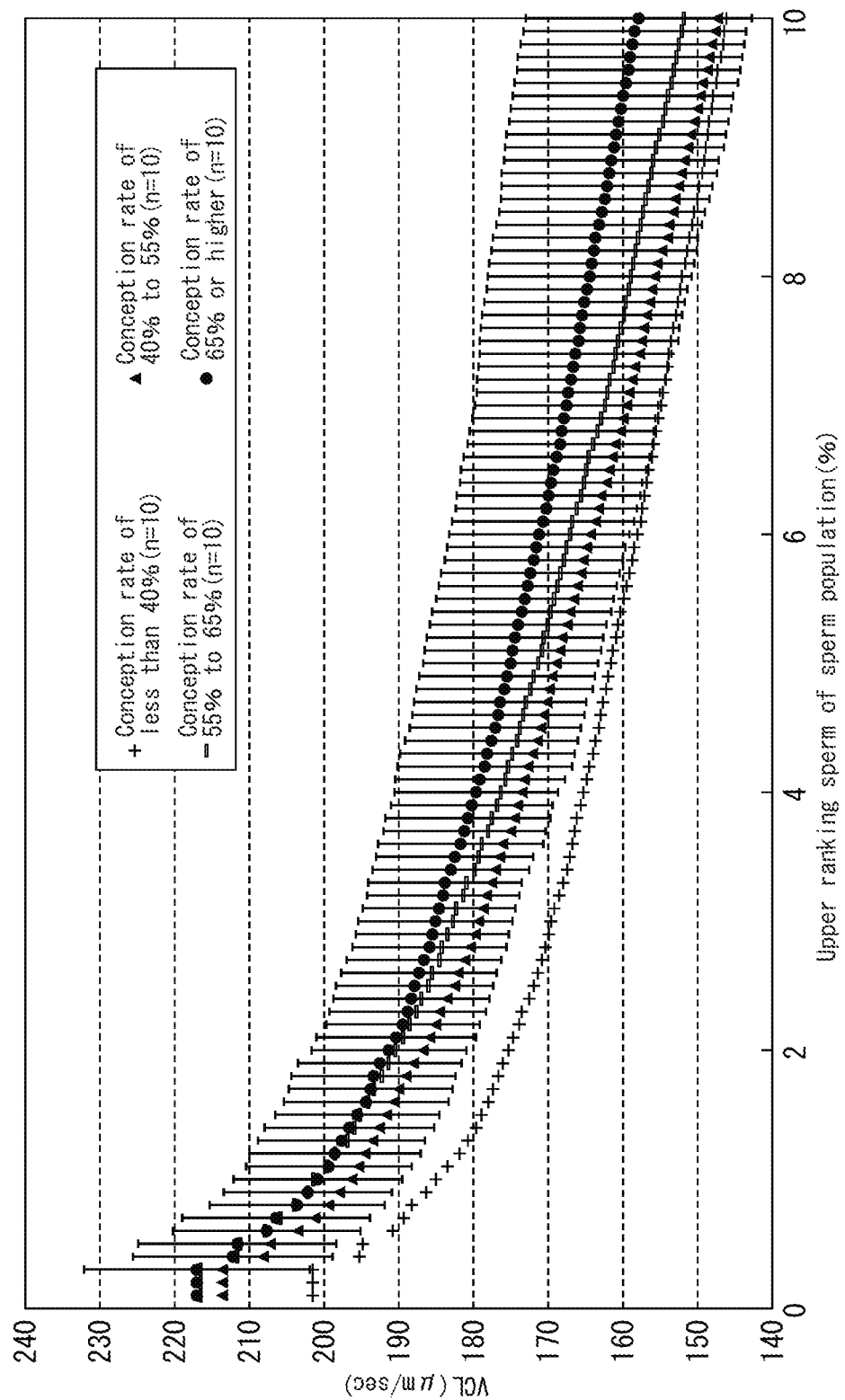

FIG. 12B is graph showing the VCL values of sperm in the upper 10% for each category of conception rate arranged in descending order as determined by measuring 3 lots each of sperm of 40 bulls having known conception rates. Values are indicated as mean values. Standard deviation is shown only for the group having a conception rate of 65% or more. Sperm fertility can be evaluated by comparing VCL values in the upper 10% or higher. When considering standard deviation, sperm fertility can be evaluated with high accuracy by comparing VCL values of 5% or more or 3% or more.

Figure 13:
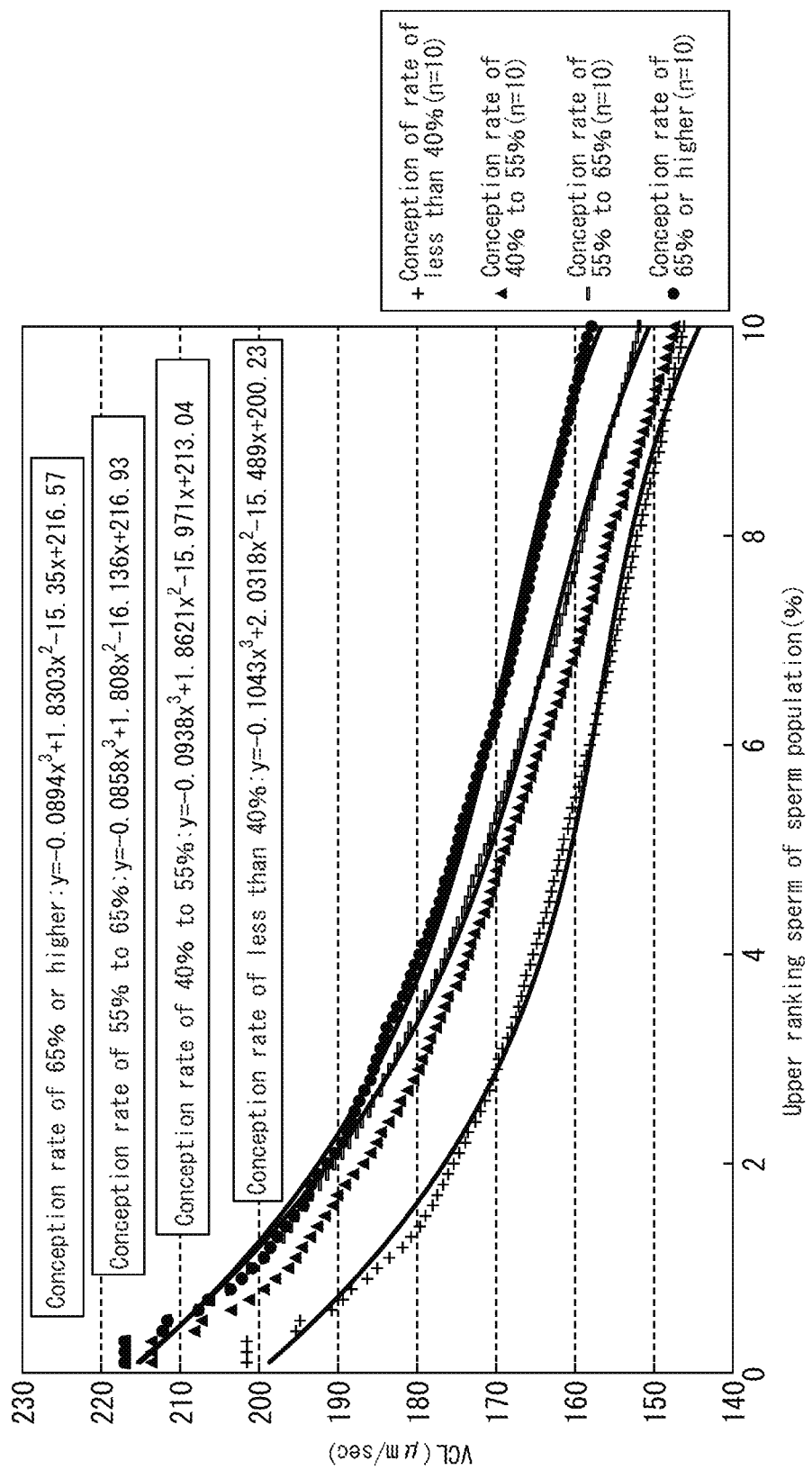

FIG. 13 is a graph showing approximation lines representing cubic approximations of graphs obtained by arranging the VCL values of all sperm for each category of conception rate in descending order as determined by measuring 3 lots each of sperm of 40 bulls having known conception rates. Sperm fertility can be evaluated with high accuracy by comparing y-intercept values of an approximation line.

Figure 14:
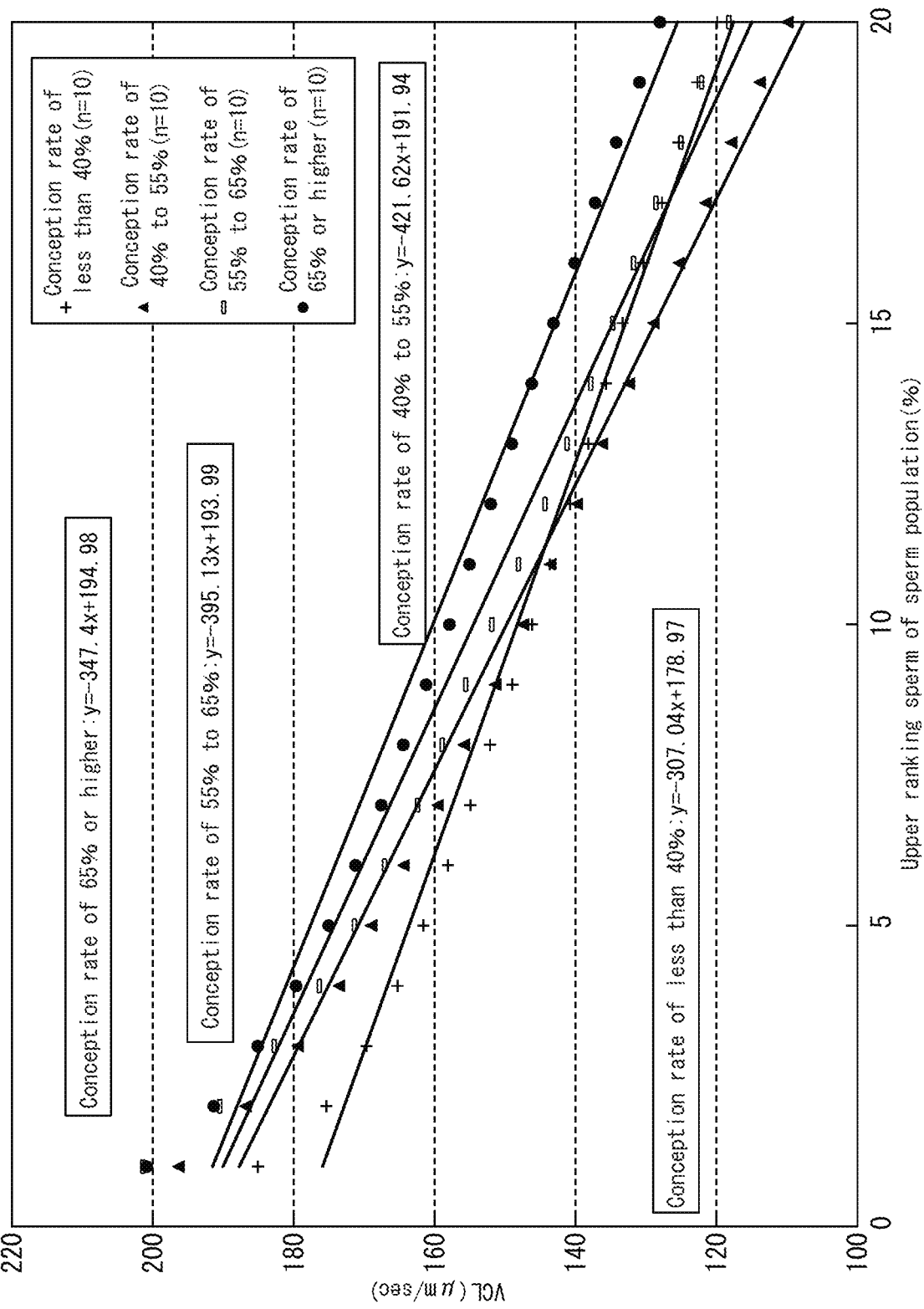

FIG. 14 is a graph showing approximation lines representing linear approximations of graphs obtained by arranging the VCL values of all sperm for each category of conception rate in descending order as determined by measuring 3 lots each of sperm of 40 bulls having known conception rates. Sperm fertility can be evaluated with high accuracy by comparing slope values of an approximation line.

Figure 15:
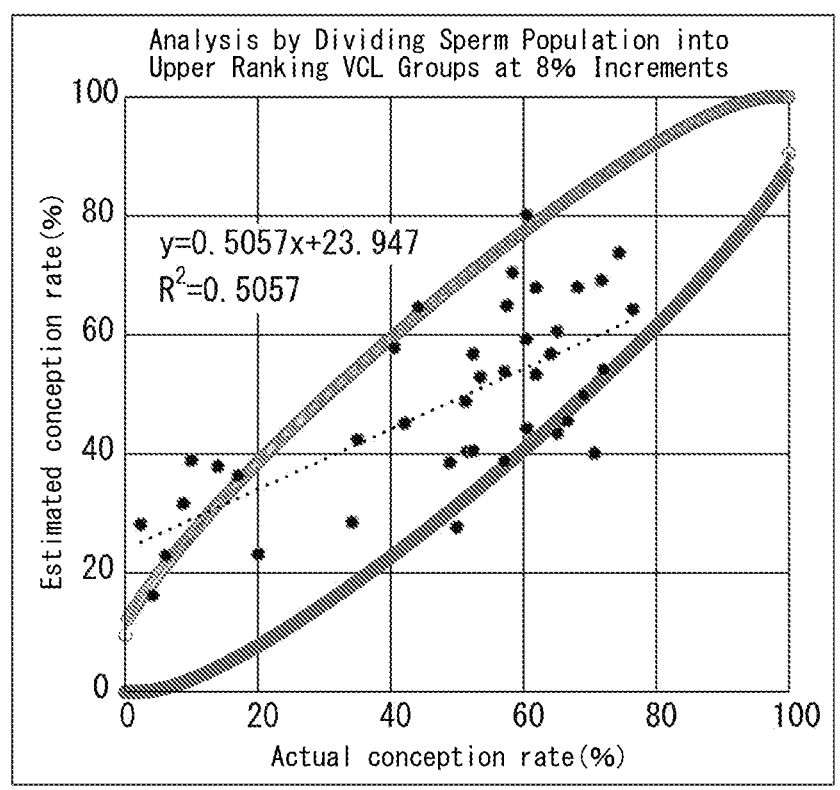

FIG. 15 shows the correlation between actual conception rate and estimated conception rate as calculated from equations obtained by measuring 3 lots each of sperm of 40 bulls having known conception rates, dividing the VCL values of a sperm population into nine groups, and carrying out multiple regression analysis on those values (r=0.7111, P<0.001). The curves indicate the upper and lower 95% confidence intervals in the case of artificially inseminating 30 animals.

Figure 16:
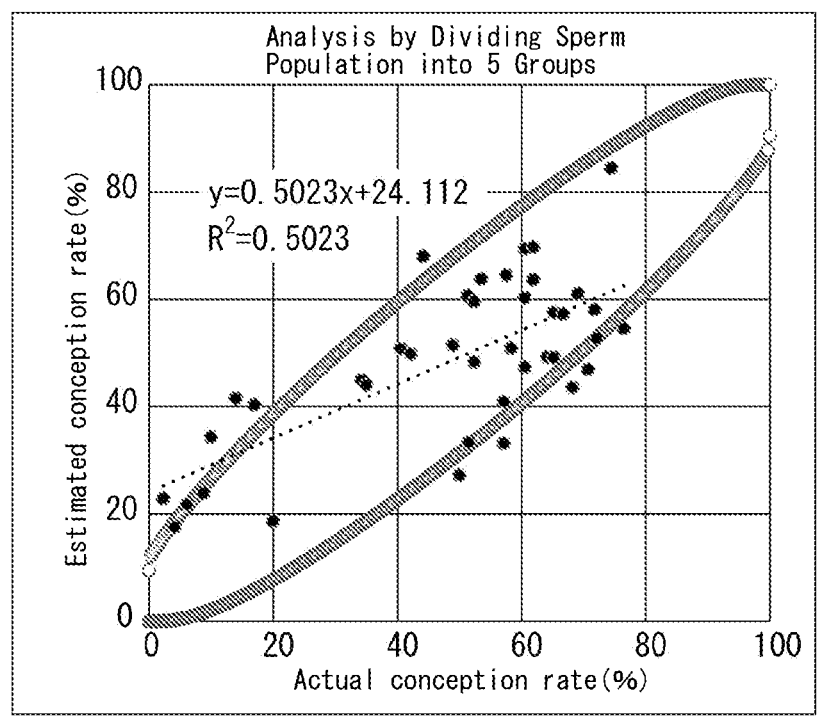

FIG. 16 shows the correlation between actual conception rate and estimated conception rate as calculated from equations obtained by measuring 3 lots each of sperm of 40 bulls having known conception rates, dividing the VCL values of a sperm population into five groups, and carrying out multiple regression analysis on those values (r=0.7087, P<0.001). The curves indicate the upper and lower 95% confidence intervals in the case of artificially inseminating 30 animals.

Figure 17:
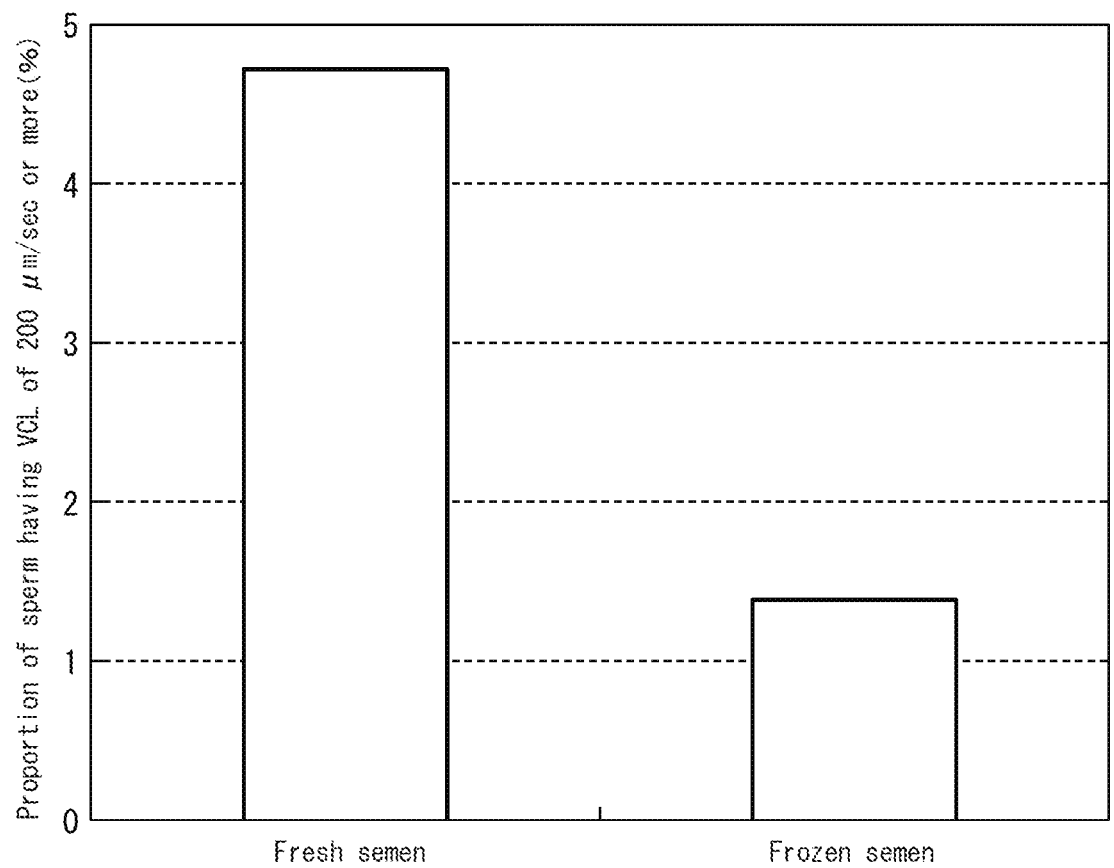

FIG. 17 is a graph showing the proportion of sperm having VCL of 200 μm/sec or more in fresh semen and frozen semen. Values are indicated as mean values (n=15). The frozen semen exhibited a significant decrease in the proportion of sperm having VCL of 200 μm/sec or more in comparison with the fresh semen (paired t-test, p<0.01).

BEST MODE FOR CARRYING OUT THE INVENTION

The present invention relates to a sperm inspection method and inspection device for evaluating sperm quality by using a high quality indicator of a sperm population, a control program that allows an information processing device to determine sperm quality, and a computer-readable medium that encodes the control program. The following provides an explanation of embodiments of the sperm inspection method and sperm inspection device according to the present invention.

Embodiment 1

The sperm inspection method of the present invention is comprised of the steps indicated below.

(1) Step for Measuring the Value of a Sperm Quality Indicator (S100)

This is a step for measuring the value of a quality indicator of individual sperm by suspending a sperm population in an inspection liquid.

(2) Step for Evaluating Sperm Quality (S200)

This is a step for evaluating sperm quality based on the value of a high quality indicator of a sperm population.

(1) The step for measuring the value of a sperm quality indicator may further comprise the following steps:

(1-1) a step for measuring the value of a sperm quality indicator based on a plurality of images of the sperm (S101), and (1-2) a step for measuring the value of a sperm quality indicator based on a plurality of images (S102). The step for measuring a quality indicator value (S100) can also be omitted by carrying out a step for reading a preliminarily acquired and stored quality indicator value.

(2) The step for evaluating sperm quality further comprises at least one, and preferably all, of the following steps:

(2-1) a step for stratifying the sperm population based on a quality indicator value (S201), (2-2) a step for calculating a quality determination value from the quality indicator value of the stratified sperm population (S202), and (2-3) a step for determining sperm quality from the quality determination value (S203).

A step (3) for arbitrarily outputting sperm quality (S300) may also be comprised after the step (2) for evaluating quality.

The method according to Embodiment 1 of the present invention may be carried out manually by a sperm laboratory technician or researcher and the like, may be carried out automatically by an inspection device or an information processing device installed with the control program of the present invention, or may be carried out semi-automatically.

Sperm derived from an arbitrary animal can be used for the sperm provided for use in the sperm inspection method of the present invention. Examples of animals include any mammals, including humans, such as livestock animals, pet animals, zoo animals and experimental animals. Examples of livestock animals include bulls, pigs, goats, horses and sheep. Examples of pet animals include dogs, cats and rabbits. Examples of zoo animals include pandas and other species for which there is the risk of extinction. Examples of experimental animals include mice, hamsters, rats, sea urchins and starfish. Any sperm derived from the testes, epididymis, ejaculated semen, stem cells, testicular stem cells, iPS cells or cultured cells and the like can be used for the sperm. In addition, the sperm may be that placed in refrigerated storage or frozen storage. The sperm is preferably that from fresh semen or frozen semen, and reflects quality immediately prior to use in artificial insemination, in vitro fertilization or microinsemination and the like.

Examples of methods used to collect sperm include a method consisting of harvesting a testis and aspirating the sperm in the case of sperm derived from the testes, a method consisting of harvesting the epididymis and aspirating the sperm in the case of sperm derived from the epididymis, a method consisting of collecting sperm after having been ejaculated into a female body or a method consisting of harvesting sperm using electrical stimulation or an artificial vagina in the case of sperm derived from ejaculated semen, and a method consisting of recovering sperm by cell culturing in the case of stem cells, testicular stem cells, iPS cells or cultured cells. The collected sperm may be suspended in seminal plasma immediately after acquisition or may be further diluted or washed with an aqueous solution and the like.

The sperm population of the present invention contains a plurality of sperm. In the case of acquiring sperm using the aforementioned sperm acquisition methods, sperm is normally recovered in the form of a sperm population. The sperm population contains sperm sub-populations after having selected or acquired a portion of the sperm population. Examples of selecting a sperm sub-population include selecting a sperm population in which sperm motility is equal to or greater than a certain value or within a certain range as measured with a sperm motility analyzer, a viable sperm population as measured with a flow cytometer or Nucleocounter, and a sperm population in which the quality of sperm constituent proteins is equal to or greater than a certain value or within a certain range as measured with a flow cytometer or fluorescence microscope, based on the results of measuring a sperm quality indicator. Examples of isolating a sperm sub-population include isolating a sperm population after having collected X sperm or Y sperm with a flow cytometer, and isolating a sperm population after having collected motile sperm by the swim-up method or a method using glass beads. In one aspect thereof, sperm included in the sperm population are preferably viable sperm.

The quality indicator of the present invention is an indicator for assessing the quality of individual sperm of a sperm population. Examples of quality indicators include indicators such as by evaluating sperm motility, sperm viability, mitochondria activity, acrosome integrity or sperm morphology normality, enabling cells to be arbitrarily evaluated molecular biologically or biochemically by lectin staining or immunofluorescence. These quality indicators can normally be measured using a sperm motility analyzer, high-speed camera, microscope such as a phase-contrast microscope, differential interference microscope, polarizing microscope, fluorescence microscope, confocal laser scanning microscope, transmission electron microscope or scanning electron microscope, flow cytometer, Nucleocounter, luminometer, absorbance reader, fluorescence reader, fluorescence polarization reader or chemiluminescence reader.

Figure 1:
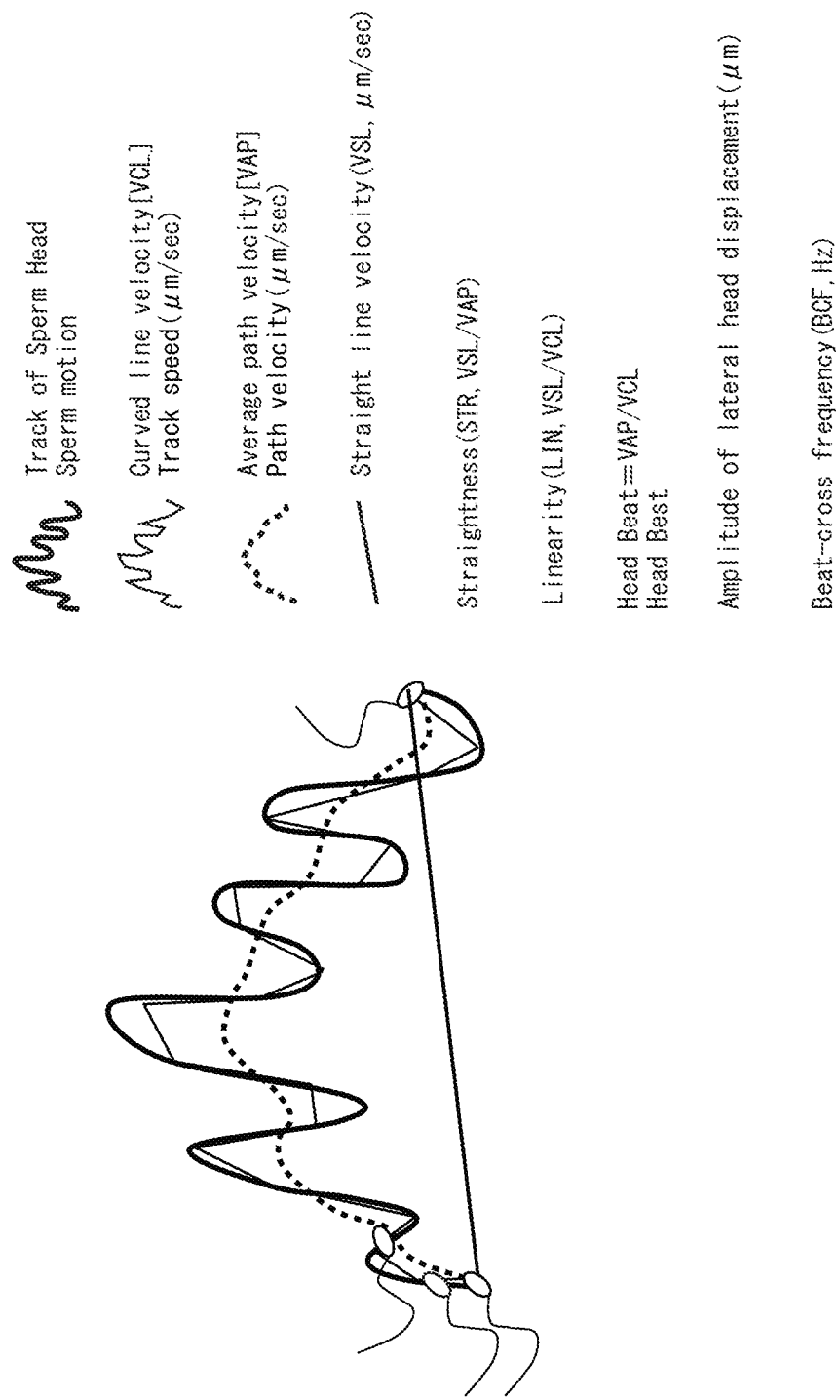
FIG. 1 is a drawing for explaining parameters used to analyze sperm motility capable of serving as a quality indicator.

Sperm motility is preferably used for the quality indicator of the present invention. Indicators such as VSL (straight line velocity, µm/sec), VAP (average path velocity, µm/sec), VCL (curvilinear velocity, µm/sec), ALH (amplitude of lateral head displacement, µm/sec), STR (straightness, VSL/VAP), LIN (linearity, VSL/VCL) and/or BCF (beat-cross frequency, Hz) can be measured by computer-assisted sperm analysis (CASA) or a high-speed camera and the like, and each value is determined according to the frame rate during image capturing. The acquired frame rate may be an arbitrary value, and an arbitrary frame rate of 10 to 2000 frames/sec typically used when observing sperm can be used, examples of which include 30 frames/sec, 60 frame/sec, 100 frames/sec, 500 frames/sec or 1000 frames/sec. In addition to being described in FIG. 1, these parameters are explained in Non-Patent Document 5 (Kinukawa, M., Doctorate Thesis, http://hdl.handle.net/2261/119 (2005)). VAP, ALH and/or BCF can be preferably used as indicators of sperm motility. Among these indicators, VAP, VCL and ALH are each involved with sperm motility, and although their values mutually differ, they demonstrate the same trend provided they relate to population distribution. Among the sperm motility indicators used in the present invention, VCL is an indicator of the velocity at which sperm actually move along their trajectory, while VAP is an indicator of the velocity over a path obtained by smoothing that trajectory. A value of 100 µm/sec or more, for example, is used in the case of using VAP as an indicator of sperm motility, a value of 150 µm/sec or more and preferably 200 µm/sec or more, for example, is used in the case of using VCL, a value of 9 µm or more and preferably 12 µm or more, for example, is used in the case of using ALH, and value of 10 to 40 Hz and preferably 20 to 30 Hz, for example, is used in the case of using BCF.

In the case of using sperm motility for the quality indicator of the present invention, a quality indicator relating to sperm motility can also be used. Examples of quality indicators include sperm flagellum movement, sperm intracellular concentrations of cAMP or calcium, the quality and amounts of sperm constituent proteins such as dynein, adenylate cyclase, adenylate kinase, protein kinase or protein phosphatase, and changes in cell membrane properties relating to capacitation or acrosome reaction that occur in parallel with sperm hyperactivation.

An arbitrary solution can be used for the inspection liquid of the present invention provided it allows evaluation of the quality of individual sperm of a sperm population. The solution is normally an aqueous solution. If the sperm is derived from the testes, epididymis, ejaculated semen, stem cells, testicular stem cells, iPS cells or cultured cells and the like, the liquid recovered with the sperm can be used as is for the inspection liquid. The inspection liquid is preferably composed of an aqueous solution containing a buffer, sugar and/or salt. More preferably, the inspection liquid is a liquid present in the female reproductive tract environment, such as the ampulla of the fallopian tube, or liquid that mimics that environment. Mimicking the female reproductive tract environment refers to mimicking the environment in which sperm reaches insemination within the female reproductive tract or mimicking liquid present therein. Examples thereof include cilia-generated flow, cervical mucus, highly viscous liquid surrounding the ova, and liquid mimicking the components or pH of oviductal fluid or follicular fluid.

The pH of the inspection liquid of the present invention may be any pH provided it allows sperm quality to be evaluated, and is normally 6.0 to 9.0. The pH is preferably 7.2 to 8.2 and more preferably 7.4 to 8.2. The concentrations of components in the inspection liquid of the present invention are determined so that the pH of the aqueous solution is within the aforementioned ranges.

Although the osmotic pressure of the inspection liquid of the present invention may be any osmotic pressure provided it allows sperm quality to be evaluated, it is normally 230 to 400 mmol/kg (mOsm/kg). This range has been identified as being the range over which sperm motility can be maintained according to the description of Non-Patent Document 6 (Guthrie, et al, Biology of Reproduction 67, 1811-1816 (2002)). Osmotic pressure of the aqueous solution is preferably 250 to 350 mmol/kg (mOsm/kg) and more preferably 260 to 320 mmol/kg (mOsm/kg). Although the theoretical value of osmotic pressure can be calculated from solute concentration, degree of dissociation and the like, it is determined using an osmotic pressure gauge (osmometer) in consideration of such factors as interaction among substances composing the solution. The concentrations of components in the inspection liquid of the present invention are determined so that osmotic pressure of the aqueous solution is within the aforementioned ranges.

The inspection liquid of the present invention can contain an arbitrary buffer provided the desired pH is achieved. Any buffer can be selected for the buffer provided it is a buffer that demonstrates buffering action in the vicinity of neutrality, and examples thereof include Good's buffers such as tris(hydroxymethyl)aminomethane, MES, HEPES, TES or tricine as well as phosphate buffer, citrate buffer and carbonate buffer. In addition, acid or base can be used in order to achieve the desired pH. Tris(hydroxymethyl)aminomethane or citric acid is used preferably. More specifically, the concentration of tris(hydroxymethyl)aminomethane is preferably 50 to 300 mM and more preferably 75 to 200 mM. The concentration of citric acid is preferably 20 to 100 mM and more preferably 25 to 75 mM.

The inspection liquid of the present invention can contain an arbitrary sugar or energy source provided it is a substance that serves as an energy source of sperm. Examples of sugars and energy sources include glucose, xylose, rhamnose, fructose, mannose, galactose, sucrose, lactose, maltose, trehalose, melibiose, raffinose, melezitose, stachyose, dextrin, N-acetyl-D-glucosamine, D-glucuronic acid, ATP and ADP. Glucose is used preferably. Glucose concentration is 5 to 100 mM and preferably 10 to 50 mM.

The inspection liquid of the present invention can contain an arbitrary salt provided it is used for the purpose of adjusting osmotic pressure. Examples of salts that can be used include chlorides, sulfates, sulfites, nitrates, acetates, gluconates, amino acid salts, citrates, carbonates and bicarbonates. Chlorides are used preferably. Sodium chloride is used more preferably. More specifically, the concentration of sodium chloride is 50 to 200 mM, preferably 50 to 150 mM and more preferably 50 to 100 mM.

The inspection liquid of the present invention can contain an arbitrary biologically active substance such as an activator capable of activating sperm. Examples of biologically active substances include calcium, magnesium, selenium, zinc, catechins, caffeine, theophylline, pentoxifylline, procaine, lidocaine, bupivacaine, imidazole, sodium pyruvate, hypotaurine, polyphenol, L-glutamine, SOD, vitamin B2, vitamin C, vitamin E, flavonoids, spermine, β-carotene, glutathione, glutathione peroxidase, glutathione reductase, catalase, carnitine, albumin, transferrin, ceruloplasmin, glucose phosphate D-hydrogenase, cholesterol, fatty acids, phosphatidylcholine and ATP. As a result of containing an activator, sperm motility and the like is activated, thereby making values of sperm quality evaluation more conspicuous during evaluation. For example, the concentration of procaine is normally 0.1 to 40 mM, the concentration of caffeine is normally 0.1 to 40 mM, and the concentration of theophylline is normally 0.1 to 40 mM.

The inspection liquid of the present invention can contain an arbitrary loading agent for the purpose of applying a load such as viscosity to sperm motility. Examples of loading agents that can be used include polyvinylpyrrolidone, methyl cellulose, ficoll, polyacrylamide, polyvinyl alcohol, alginic acid, alginic acid salts, hyaluronic acid, hyaluronic acid salts and gelatin. Polyvinylpyrrolidone K-90 is used preferably. More specifically, the concentration of polyvinylpyrrolidone K-90 is 0.5 to 16% (w/v) and preferably 1 to 8% (w/v).

The inspection liquid of the present invention can contain an arbitrary antibiotic for the purpose of preventing bacterial growth. Examples of antibiotics include penicillin, streptomycin, gentamycin and dibekacin. Moreover, preparation of the inspection liquid can include a sterilization procedure for preventing bacterial growth. Examples of sterilization procedures include treating the inspection liquid with a filter having a pore diameter of 0.2 μm or 0.45 μm, and sterilizing the inspection liquid in an autoclave.

Any method can be used to suspend sperm in the inspection liquid of the present invention provided the inspection liquid can be transferred. For example, the sperm can be suspended in the inspection liquid using a manual pipette, automatic pipette or dispenser.

The duration of suspending sperm in the inspection liquid of the present invention may be any amount of time provided it allows the value of a sperm quality indicator to be measured. For example, in the case of evaluating sperm motility, the duration is normally from immediately after suspending to 6 hours after suspending, preferably from immediately after suspending to 3 hours after suspending, more preferably from immediately after suspending to 1 hour after suspending, and particularly preferably from immediately after suspending to 30 minutes after suspending.

The temperature at which sperm is suspended in the inspection liquid of the present invention may be any temperature provided the value of a sperm quality indicator can be measured. Normally, measurements can be made within a range of 0 to 50° C. using an incubator and the like. Measurements are made by preferably maintaining a temperature of 25 to 45° C. that is close to the body temperature of the animal from which the sperm is derived, more preferably 33 to 43° C. and particularly preferably 36 to 40° C.

The step for evaluating sperm quality of the present invention comprises stratification of a sperm population based on the value of a quality indicator.

Stratification refers to classifying sperm into two or more populations based on the value of a sperm quality indicator. Although the number of populations can be selected arbitrarily, the sperm can be classified into, for example, 2, 3, 4, 5, 6, 7, 8, 9 or 10 populations. The criteria for stratification can be arbitrarily selected based on the value of the quality indicator used, and may be selected so that the proportion of sperm or number of sperm is a certain number for each group, or sperm may be classified by setting a suitable value. For example, a sperm population can be stratified in a form such that the value of the quality indicator of that sperm population is for every upper 20%, every upper 10%, every upper 5%, every upper 3% or every upper 1%, or the sperm population can be stratified such that the value of the quality indicator of that sperm population is within the upper 80%, within the upper 50%, within the upper 30%, within the upper 10%, the upper 20 to 80%, the upper 10 to 50% or the upper 1 to 5%. In a different aspect, a sperm population can also be stratified based on the value of a quality indicator in the sperm population. For example, in the case the quality indicator is VCL, the sperm population can be stratified over a range of 200 μm/sec or more, 100 μm/sec or more, 175 to 200 μm/sec, 150 to 200 μm/sec, 100 to 150 μm/sec or 0 to 75 μm/sec. Among each of the populations stratified in this manner, a quality determination value can be calculated from the value of a quality indicator in all groups, or a quality determination factor can be calculated from the value of a quality indicator of one or more arbitrarily selected groups in each of the populations. In one aspect thereof, among each of the stratified populations, a quality determination value can be calculated from the mean, median or mode of the quality indicator of a high quality group.

The value of a quality indicator of a higher group of a sperm population of the present invention is normally a value within 50%, preferably within 10%, more preferably within 5%, even more preferably within 3%, still more preferably within 1% and more preferably still within 0.3% from a high value of a sperm quality indicator within a sperm population provided the sperm has been acquired by a method for collecting sperm as previously described. These values are particularly preferably predicted from a graph determined by arranging the values of a sperm quality indicator of individual sperm in order. The sperm population may consist of all sperm suspended in the inspection liquid, or sperm present in a certain region may be selected arbitrarily. However, the scale of the high quality indicator value can be arbitrarily changed according to the sperm population. For example, since there are cases in which sperm having a high quality indicator value of a sperm population acquired from ejaculated semen and the like is selectively acquired in the case of a sperm sub-population after having selected or isolated a portion of the sperm population, the values of all sperm of the sperm population are used.

Evaluation of sperm quality based on a quality indicator value refers to stratify the aforementioned sperm population based on a quality indicator value, determining a quality determination value from the quality indicator value of the stratified sperm population, and determining quality from the quality determination value. The quality determination value is selected from the group consisting of:

(1) the mean, median or mode of a quality indicator value of the stratified population, (2) the proportion or number of sperm having a reference value that exceeds or is within a certain range of a reference value of a prescribed quality indicator in the stratified population, and (3) an approximation line, intercept, coefficient or slope obtained from a graph in which the quality indicator values of individual sperm of the stratified population are arranged in order. The aforementioned (1) to (3) can each be combined. Sperm quality can be evaluated by comparing quality determination values between samples of a sperm population, by comparing with a reference value of a quality indicator for which the correlation with fertility or other sperm quality has been indicated in advance, or by applying to an estimation equation calculated using a plurality of semen for which fertility has been determined in advance.

The following provides a detailed explanation of a method for determining sperm quality using the aforementioned quality determination values of (1) to (3).

(1) Case of Quality Determination Value being the Mean, Median or Mode of a Quality Indicator Value of a Stratified Population As one example of this case, although VCL is used for the quality indicator and 10% is selected as the high quality group, the quality indicator and stratified population are not intended to be limited thereto. The step for evaluating sperm quality based on the quality indicator value is carried out in the manner indicated below:

a high quality group of the upper 10% of a sperm population is selected based on a quality indicator value (VCL), the mean, median or mode of the quality indicator value (VCL) of the high quality group is calculated, and sperm quality is determined based on the mean, median or mode of VCL.

The fertility of that sperm population can be determined by comparing the calculated mean, median or mode with a quality indicator reference value, such as 200 μm/sec, 175 μm/sec or 150 μm/sec, for which correlation with fertility has been indicated in advance. In addition, sperm quality can also be determined by applying the calculated mean, median or mode of VCL to an estimation equation indicating the relationship between fertility and the mean, median or mode of VCL of a high quality group in the upper 10%.

(2) Case of Quality Determination Value being the Proportion or Number of Sperm Having a Reference Value that Exceeds or is within a Certain Range of a Reference Value of a Prescribed Quality Indicator in the Stratified Population As an example of this case, although VCL is used for the quality indicator and 200 μm/sec is selected for the quality indicator reference value, the quality indicator and reference value are not intended to be limited thereto. The step for evaluating sperm quality based on the quality indicator value is carried out in the manner indicated below:

a high quality group having a quality indicator value (VCL) that exceeds the reference value (200 μm/sec) of the quality indicator value (VCL) is selected, the number or proportion of sperm of the high quality group is calculated; and sperm quality is determined based on the number or proportion of sperm.

The fertility of the sperm population can be determined by comparing the calculated number or proportion of sperm with the number or proportion of sperm which correlation with fertility has been indicated in advance. In addition, the fertility of that sperm population can also be determined by applying the number or proportion of sperm to an estimation equation indicating the relationship between fertility and the number or proportion of sperm calculated using a plurality of semen for which fertility has been determined in advance.

(3) Case of Approximation Line, Intercept, Coefficient or Slope Obtained from a Graph in which the Quality Indicator Values of Individual Sperm of the Stratified Population are Arranged in Order As an example of this case, although VCL is used for the quality indicator and 10% is selected for the high quality group, the quality indicator and high quality group are not intended to be limited thereto. The step for evaluating sperm quality based on the quality indicator value is carried out in the manner indicated below:

a high quality group of the upper 10% of a sperm population is selected based on the quality indicator value (VCL), the quality indicators values (VCL) of the high quality group are arranged in ascending or descending order, quality indicator values are plotted on the Y axis, rank is plotted on the X axis, and the approximation line, intercept, coefficient or slope of the resulting graph is calculated, and sperm quality is determined based on the approximation line, intercept, coefficient or slope. Intercept, coefficient or slope can also be determined from the approximation line. Furthermore, the plots on the X axis and Y axis may also be reversed. The approximation line is a formula for ascertaining an outline in the case of having arranged the sperm quality values of individual sperm in order, and examples thereof include linear approximation, polynomial approximation, exponential approximation, logarithmic approximation, power approximation, moving average, asymptote and tangent. Arranging in order refers to arranging the values of individual sperm in ascending or descending order, and an approximation line can be determined by arranging the sperm of a high quality group, such as an upper 30% or higher group, preferably an upper 20% or higher group, more preferably a 10% or higher group and even more preferably an 8% or higher group. The approximation line is mainly represented as a straight line, function, logarithm, exponent, or sigmoid curve by carrying out regression analysis using a statistical technique such as the least-squares method and calculating a regression formula. The use of such an approximation line makes it possible to obtain a predicted value of fertility. In addition, predicted values can be determined using the intercept, coefficient or slope of an approximation line. Moreover, in the case of, for example, using a plurality of quality indicators in the manner of VCL and ALH as references, an estimation equation of fertility can be calculated by carrying out multivariate analysis such as multiple regression analysis.

As has been previously described, the stratified population used in (1) to (3) may be examined with respect to a high quality group, or may be examined in terms of a quality indicator value of a high quality group while adding an examination of a quality indicator value of another group. In addition, in a different aspect, a quality determination value can be calculated based on the quality indicator value of not only a high quality group, but also another group. In the case of calculating a quality determination value based on a quality indicator value of one group followed by calculating a quality determination value based on the quality indicator value of another group, the same quality determination value as that used in the aforementioned (1) to (3) can be used for the quality determination value or a different quality determination value can be used. The following provides an explanation of examples of calculating a quality determination value.

(1) Case in which Quality Determination Value is Mean, Median or Mode of Quality Indicator Value of a Stratified Population As one example of this case, although VCL is used for the quality indicator and groups obtained by dividing the quality indicator value of the upper 80% into 10% increments are used for the stratified sperm population, the quality indicator value and each sperm population group are not intended to be limited thereto. The step for evaluating sperm quality based on quality indicator value is carried out in the manner indicated below:

8 groups are selected based on the quality indicator value (VCL) that are obtained by dividing the upper 80% of a high quality group of a sperm population into 10% increments, the mean, median or mode of the quality indicator value is calculated for each of the 8 groups, and sperm quality is determined based on the mean, median or mode of each VCL.

The fertility of that sperm population can be determined by comparing each calculated mean, median or mode with a reference value, such as 200 μm/sec, 175 μm/sec or 150 μm/sec, for which fertility has been preliminarily indicated. In addition, sperm quality can be determined by applying the calculated mean, median or mode of VCL to an estimation equation indicating the relationship between fertility and the mean, median or mode of the VCL of the 8 groups obtained by dividing the entire sperm population into 10% increments determined in advance, or by using an estimation equation calculated by carrying out multivariate analysis such as multiple regression analysis.

(2) Case in which Quality Determination Value is the Proportion or Number of Sperm of a Reference Value that Exceeds or is within a Certain Range of a Reference Value of a Prescribed Quality Indicator Value in a Stratified Population As an example of this case, although VCL is selected for the quality indicator and 200 μm/sec or more, 150 to 200 μm/sec, 100 to 150 μm/sec and 50 to 100 μm/sec are selected for the stratification reference values, the quality indicator value and stratification reference values are not intended to be limited thereto. The step for evaluating sperm quality based on the quality indicator value is carried out in the manner indicated below:

4 groups are selected that are obtained by dividing reference values of the quality indicator value (VCL) into 200 μm/sec or more, 150 to 200 μm/sec, 100 to 150 μm/sec and 50 to 100 μm/sec, the number or proportion of sperm is calculated for each of the 4 groups, and sperm quality is determined based on each number or proportion of sperm.

The fertility of that stratified population can be determined by comparing the calculated number or proportion of sperm with the number or proportion of sperm for which the correlation with fertility has been indicated in advance. In addition, the fertility of that sperm population can be determined by applying the number or proportion of sperm to an approximation line of fertility and the number or proportion of sperm calculated using a plurality of semen for which fertility has been determined in advance, or by applying to an estimation equation calculated by carrying out multivariate analysis such as multiple regression analysis.

(3) Case in which Quality Determination Value is an Approximation Line, Intercept, Coefficient or Slope Obtained from One or a Plurality of Graphs Determined by Arranging the Quality Indicator Values of Individual Sperm of a Sperm Population in a Stratified Population in Order As an example of this case, although VCL is used for the quality indicator and the case of dividing the quality indicator value of the upper 80% into 10% increments is selected for the stratified sperm population, the quality indicator value and each sperm population group are not intended to be limited thereto. The step for evaluating sperm quality based on quality indicator value is carried out in the manner indicated below:

Eight groups are selected by dividing the quality indicator value of high quality group of the upper 80% into 10% increments based on the quality indicator values (VCL), quality indicator values are plotted on the Y axis, rank is plotted on the X axis, and the approximation line, intercept, coefficient or slope of the resulting graph is calculated, and sperm quality is determined based on the approximation line, intercept, coefficient or slope. Intercept, coefficient or slope can also be determined from the approximation line. Furthermore, the plots on the X axis and Y axis may also be reversed. The approximation line is a formula for ascertaining an outline in the case of having arranged the sperm quality values of individual sperm in order, and examples thereof include linear approximation, polynomial approximation, exponential approximation, logarithmic approximation, power approximation, moving average, asymptote and tangent. Arranging in order refers to arranging the values of individual sperm in ascending or descending order. The approximation line is mainly represented as a straight line, function, logarithm, exponent, or sigmoid curve by carrying out a regression analysis using a statistical technique such as the least-squares method and calculating a regression formula. Moreover, in the case of, for example, using a plurality of quality indicators in the manner of VCL and ALH as references, an estimation equation of fertility can be calculated by carrying out multivariate analysis such as multiple regression analysis. An estimation equation calculated in this manner can be used to determine sperm quality by using an estimation equation indicating the relationship between fertility and the 8 groups obtained by dividing the entire sperm population into 10% increments, or using an estimation equation calculated by carrying out multivariate analysis such as multiple regression analysis.

Embodiment 2

Figure 2:
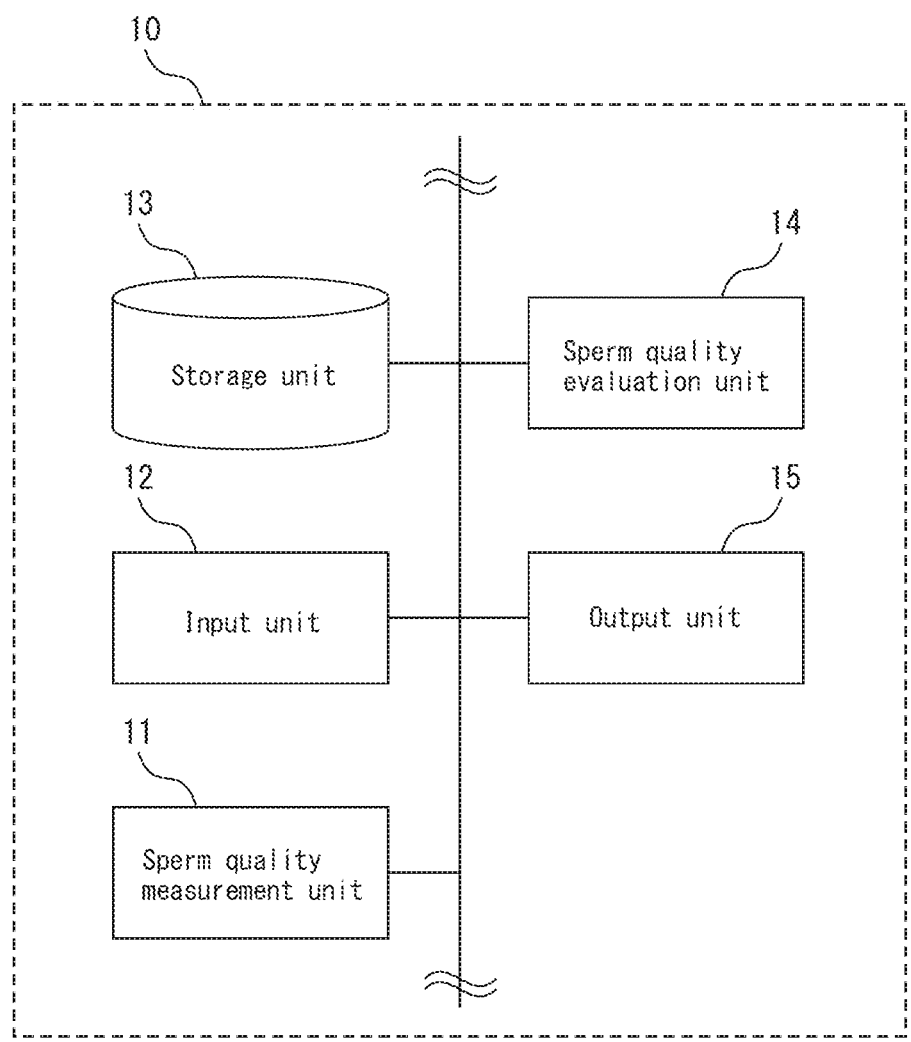
FIG. 2 is a block diagram of an inspection device according to an embodiment of the present invention.
Figure 3:
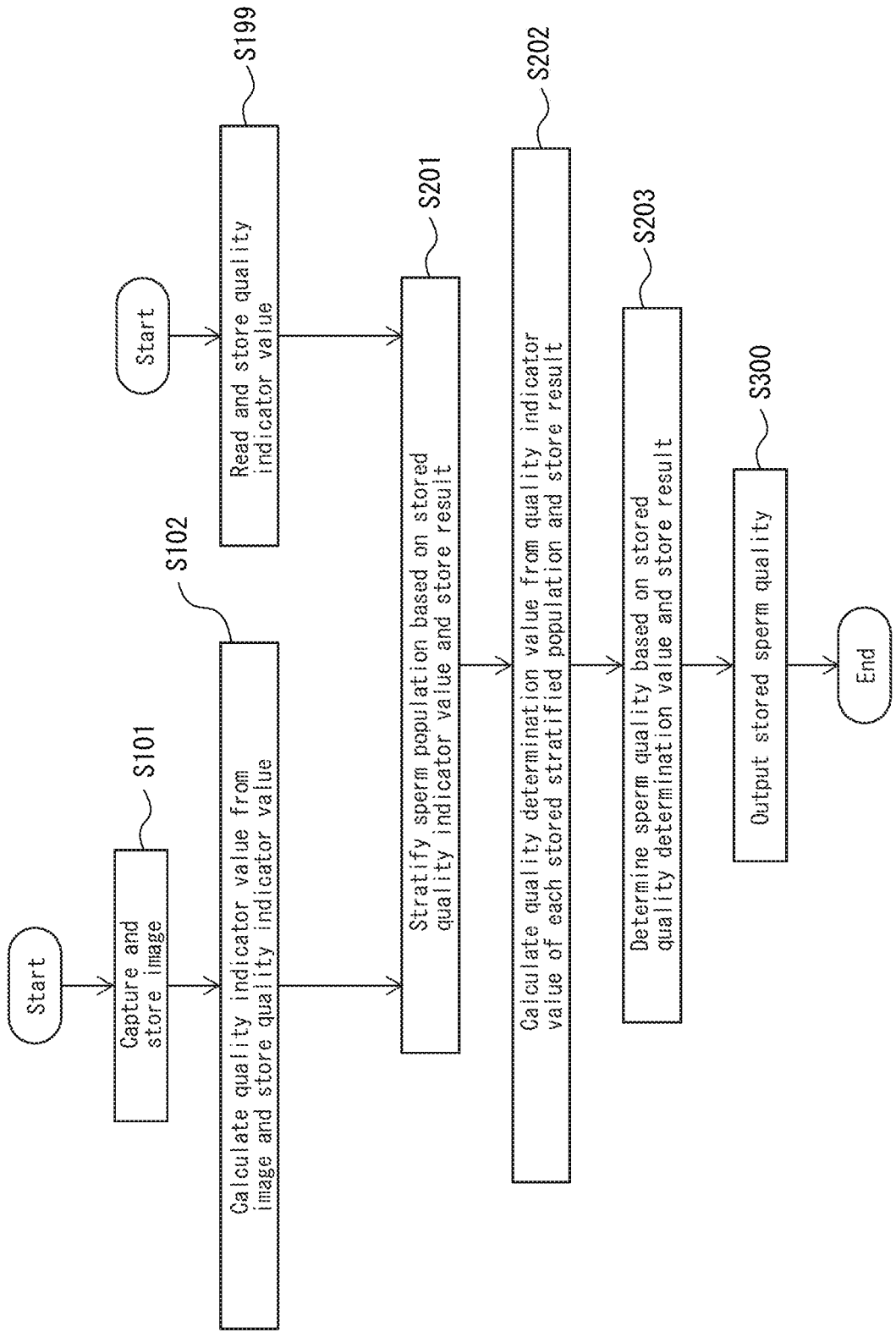
FIG. 3 is a flow chart showing an example of an operation for determining sperm quality.

The configuration of the sperm inspection device of the present invention is shown in FIG. 2. A sperm inspection device 10 is mainly provided with a sperm quality measurement unit 11 that measures the value of a sperm quality indicator (sperm quality measuring means), an input unit 12 for entering measured data or arithmetic processing instructions and the like (input means), a storage unit 13 that stores measured data or arithmetic processing results and the like (storage means), a sperm quality evaluation unit 14 that evaluates sperm quality based on the value of a measured sperm quality indicator (sperm quality evaluating means), and an output unit 15 that outputs the results of sperm quality evaluation (output means).

The sperm quality measurement unit 11 carries out a step for measuring the value of a sperm quality indicator as explained in Embodiment 1. The sperm quality measurement unit 11 is constituent site for measuring the values of a quality indicator of individual sperm of a sperm population suspended in the inspection liquid. More specifically, the sperm quality measurement unit 11 is a measuring means for measuring the value of a quality indicator of individual sperm for a sperm population that has the function of a sperm motility analyzer, high-speed camera, microscope such as a phase-contrast microscope, differential interference microscope, polarizing microscope, fluorescence microscope, confocal laser scanning microscope, transmission electron microscope or scanning electron microscope, flow cytometer, Nucleocounter, luminometer, absorbance reader, fluorescence reader, fluorescence polarization reader or chemiluminescence reader. The sperm quality measurement unit 11 may be composed separately from the sperm inspection device 10 or measured data may be input via the input unit 12 using a network or storage medium.

The input unit 12 serves as an interface and the like, and contains an operating unit such as a keyboard or mouse. As a result, the input unit 12 enables input of data measured with the sperm quality measurement unit 11 or instructions for arithmetic processing carried out with the sperm quality evaluation unit 14. In addition, in the case, for example, the sperm quality measurement unit 11 is provided externally, the input unit 12 may contain an interface and the like separate from the operating unit that enables input of measured data and the like via a network or storage medium.

The storage unit 13 has a memory device such as RAM, ROM or flash memory, a hard disk device such as a hard disk drive or a portable storage device such as an optical disk. The storage unit 13 stores instructions input from the input unit 12, arithmetic processing results acquired with the sperm quality evaluation unit 14, and a computer program or database and the like used for various processing by an information processing device. The computer program may be installed on a computer-readable card-type recording medium such as a CD-ROM or DVD-ROM or may be installed via the Internet. The computer program is installed in the storage unit 13 using a known setup program and the like.

The sperm quality evaluation unit 14 carries out a step for evaluating sperm quality as explained in Embodiment 1. The sperm quality evaluation unit 14 is a constituent site for evaluating sperm quality using a high quality indicator of a sperm population as a reference. Consequently, various types of arithmetic processing are performed on data measured with the sperm quality measurement unit 11 and stored in the storage unit 13 in accordance with a program stored in the storage unit 13. Arithmetic processing is carried out by a CPU contained in the sperm quality evaluation unit 14. This CPU is able to carry out various types of control by containing a function module that controls the sperm quality measurement unit 11, the input unit 12, the storage unit 13 and the output unit 15. Each of these units may be configured with respective and independent integrated circuits, microprocessors or firmware and the like.

The output unit 15 also includes a display device such as a liquid crystal display and an output means such as a printer. The output unit 15 outputs the results of carrying out arithmetic processing by the sperm quality evaluation unit in the form of values of the results of evaluating sperm quality, fertility indicator values or predicted fertility and the like.

The following provides a detailed explanation of the sperm inspection method and device of the present invention using the following examples. The present invention is not limited to the following examples, and can be altered or modified within the normal range of the technical field of the present invention.

Example 1

Examination of Inspection Liquid pH

Frozen semen prepared using ejaculated semen from breeding bulls from the Livestock Improvement Association of Japan, Inc. was thawed in accordance with ordinary methods and centrifuged for 5 minutes at room temperature at 2000 rpm for 10 million sperm, followed by removing the supernatant and adding to the sediment 250 µl of inspection liquid prepared by adding 140.6 mM tris(hydroxymethyl) aminomethane (Wako Pure Chemical Industries, Ltd.), 45.3 mM citric acid (Wako Pure Chemical Industries, Ltd.), 16.7 mM glucose (Wako Pure Chemical Industries, Ltd.), 79.2 mM sodium chloride (Wako Pure Chemical Industries, Ltd.), 2 mM calcium chloride (Wako Pure Chemical Industries, Ltd.), 0.3% (w/v) BSA (Wako Pure Chemical Industries, Ltd.), 650 U/ml of penicillin G potassium (Banyu Pharmaceutical Co., Ltd.) and 0.7 mg (titer)/ml of streptomycin (Meiji Pharmaceutical Co., Ltd.), and using 1 N sodium hydroxide or 1 N hydrochloric acid to adjust the pH from 6.0 to 9.0 in 0.2 increments. The inspection liquids were then incubated for 10 minutes at 38° C. Equal volumes of the aforementioned inspection liquids at each pH to which had been added 4% (w/v) polyvinylpyrrolidone K-90 (Wako Pure Chemical Industries, Ltd.) were mixed, dropped into a slide chamber (Leja B.V.) pre-warmed to 38° C. and having a thickness of 20 µm, and measured using the sperm mobility analyzer, Ceros (Hamilton Thorne, Inc.).

Figure 4:
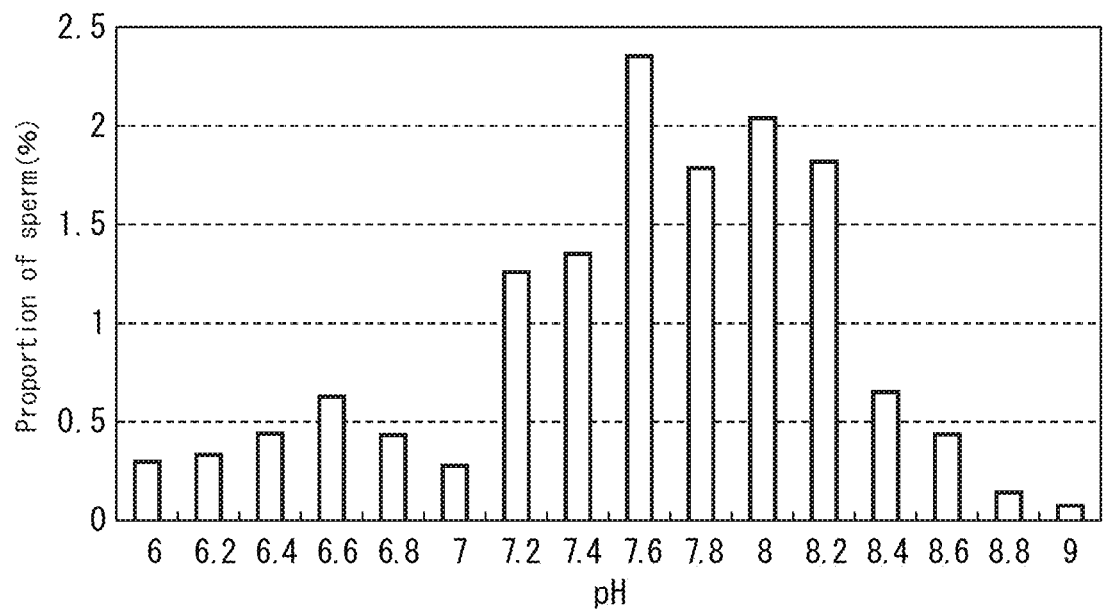
FIG. 4 is a graph showing the proportion of sperm having VCL of 200 μm/sec or more in the case of changing the pH of an inspection liquid over the range of 6.0 to 9.0 Values are indicated as mean values (n=4). Sperm having remarkably high propulsion were able to be detected at pH 7.2 to 8.2.

The measurement results are shown in FIG. 4. Measurement was possible over a range of pH 6.0 to 8.6, and sperm having high propulsion were able to be detected over a pH range of 7.2 to 8.2. The highest proportion of sperm exhibiting the highest propulsion was detected at pH 7.6.

Example 2

Examination of Suspension Time

Frozen semen prepared using ejaculated semen from breeding bulls from the Livestock Improvement Association of Japan, Inc. was thawed in accordance with ordinary methods and centrifuged for 5 minutes at room temperature at 2000 rpm for 10 million sperm, followed by removing the supernatant and adding 250 µl of the inspection liquid described in Example 1 to the sediment after adjusting the pH to 7.6. The inspection liquid was then incubated at 38° C. Equal volumes of the aforementioned inspection liquids to which were added 4% (w/v) polyvinylpyrrolidone K-90 immediately after suspending (0 minutes) or at 10, 30 and 60 minutes after suspending were mixed and then measured using the method described in Example 1.

Figure 5:
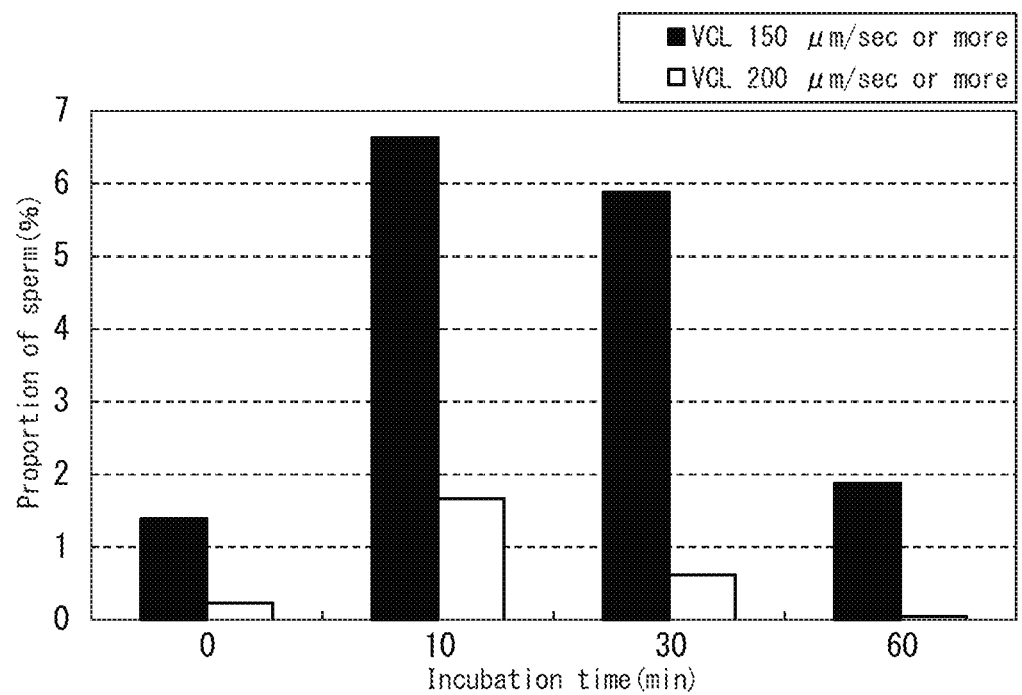
FIG. 5 is a graph showing the proportion of sperm having VCL of 150 μm/sec or more and 200 μm/sec or more in the case of changing suspension time of the inspection liquid. Values are indicated as mean values (n=6). Sperm having remarkably high propulsion were able to be detected starting immediately after suspending to 30 minutes after suspension.

FIG. 5 shows the proportions (%) of sperm having VCL of 150 µm/sec or more and 200 µm/sec or more. Sperm having high propulsion were able to be detected from immediately after to 30 minutes after suspension.

Example 3

Examination of Sperm Fertility

Frozen semen prepared using ejaculated semen from breeding bulls (n=29 or 40) from the Livestock Improvement Association of Japan, Inc. having known conception rates was thawed in accordance with ordinary methods and centrifuged for 5 minutes at room temperature at 2000 rpm for 10 million sperm, followed by removing the supernatant and adding 250 µl of the inspection liquid described in Example 2 to the sediment. The inspection liquid was then incubated for 10 minutes at 38° C. Equal volumes of the inspection liquids to which were added 4% (w/v) polyvinylpyrrolidone K-90 were mixed and then measured using the method described in Example 1. A conventional inspection example in the form of an indicator of sperm motility was indicated as the proportion (%) of sperm having VAP of 50 µm/sec or more at 38° C. using a sperm motility analyzer on sperm following freezing and thawing.

Figure 6A:
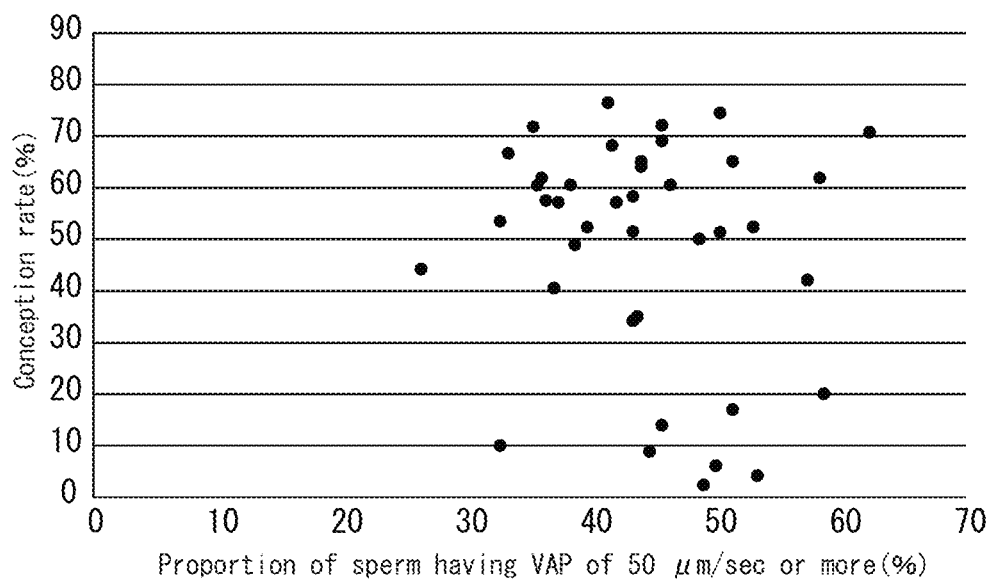
FIG. 6A is a graph showing the correlation between the proportion of sperm having VAP of 50 μm/sec or more and conception rate as determined by measuring 3 lots each of sperm from 40 bulls having known conception rates. The correlation between the proportion of sperm having VAP of 50 μm/sec or more and conception rate was not high.
Figure 6B:
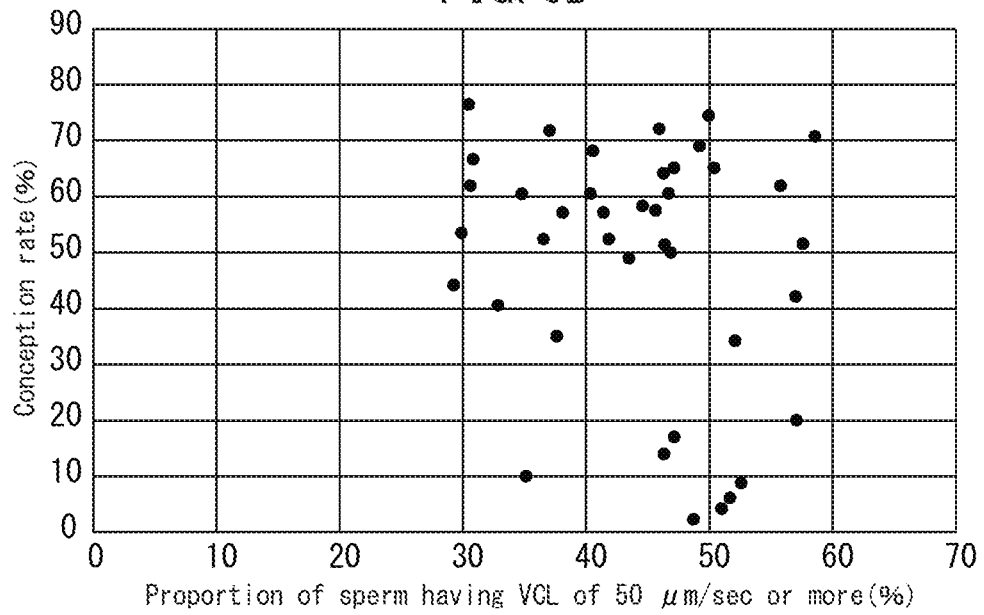
FIG. 6B is a graph showing the correlation between the proportion of sperm having VCL of 50 μm/sec or more and conception rate as determined by measuring 3 lots each of sperm from 40 bulls having known conception rates. The correlation between the proportion of sperm having VCL of 50 μm/sec or more and conception rate was not high.
Figure 6C:
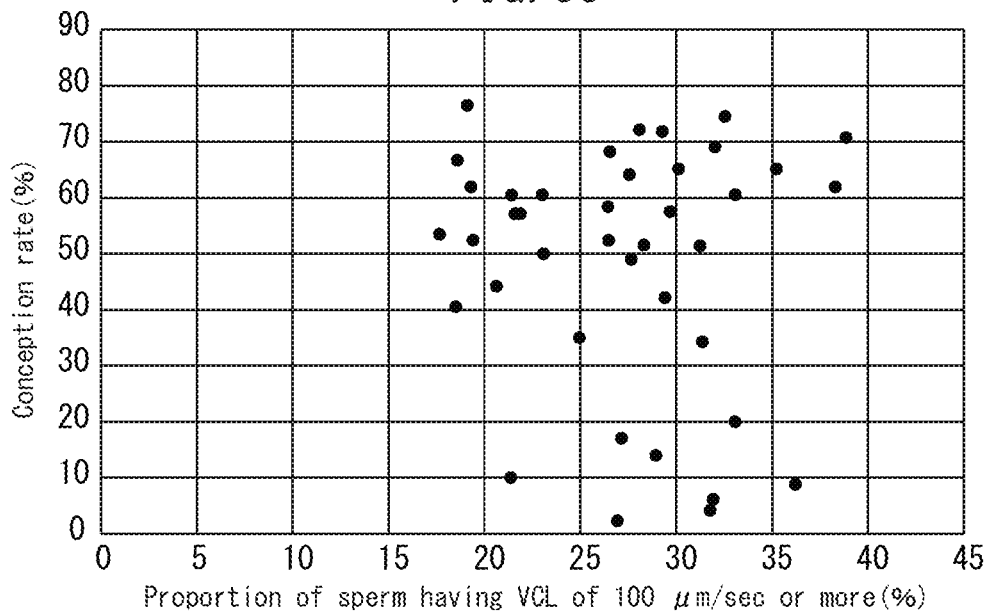
FIG. 6C is a graph showing the correlation between the proportion of sperm having VCL of 100 μm/sec or more and conception rate as determined by measuring 3 lots each of sperm from 40 bulls having known conception rates. The correlation between the proportion of sperm having VCL of 100 μm/sec or more and conception rate was not high.
Figure 6D:
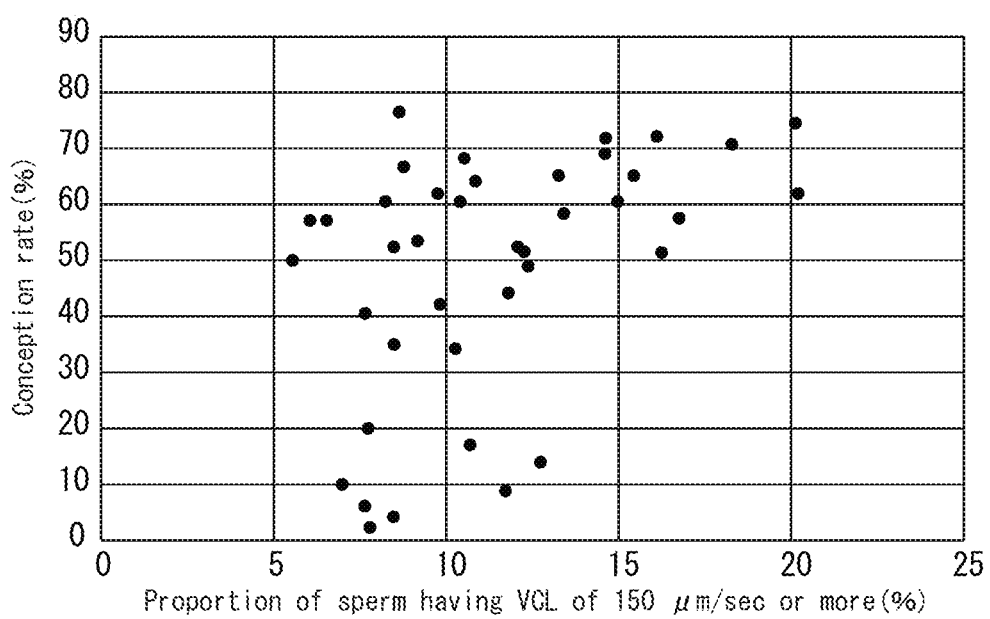
FIG. 6D is a graph showing the correlation between the proportion of sperm having VCL of 150 μm/sec or more and conception rate as determined by measuring 3 lots each of sperm from 40 bulls having known conception rates. A correlation was able to be confirmed between the proportion of sperm having VCL of 150 μm/sec or more and conception rate.
Figure 6E:
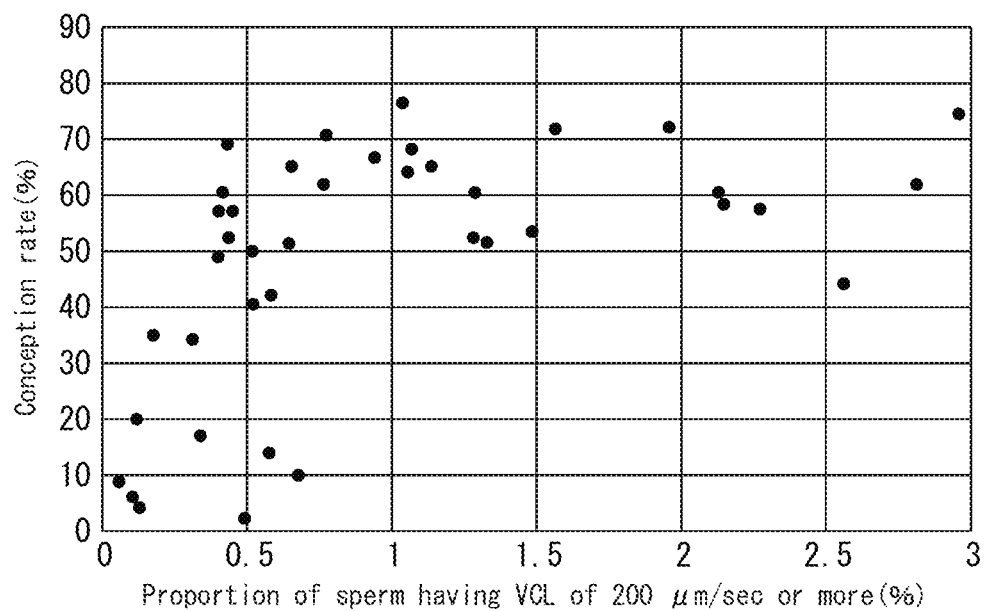
FIG. 6E is a graph showing the correlation between the proportion of sperm having VCL of 200 μm/sec or more and conception rate as determined by measuring 3 lots each of sperm from 40 bulls having known conception rates. A high correlation was able to be confirmed between the proportion of sperm having VCL of 200 μm/sec or more and conception rate.

The proportion of sperm having VAP of 50 µm/sec or more is shown in FIG. 6A. A correlation was not observed between conception rate and the conventional indicator of sperm motility. Next, the results of measuring while changing the VCL cutoff value are shown in FIGS. 6B to 6E. The proportion of sperm having VCL of 50 µm/sec or more is shown in FIG. 6B, the proportion of sperm having VCL of 100 µm/sec or more is shown in FIG. 6C, the proportion of sperm having VCL of 150 µm/sec or more is shown in FIG. 6D, and the proportion of sperm having VCL of 200 µm/sec or more is shown in FIG. 6E. In low fertility samples having a conception rate of 40% or less, the proportion of sperm was able to be confirmed to decrease as the cutoff value became higher. Consequently, conception chance was determined to be able to be predicted by detecting sperm demonstrating higher propulsion by raising the cutoff value.

Figure 7:
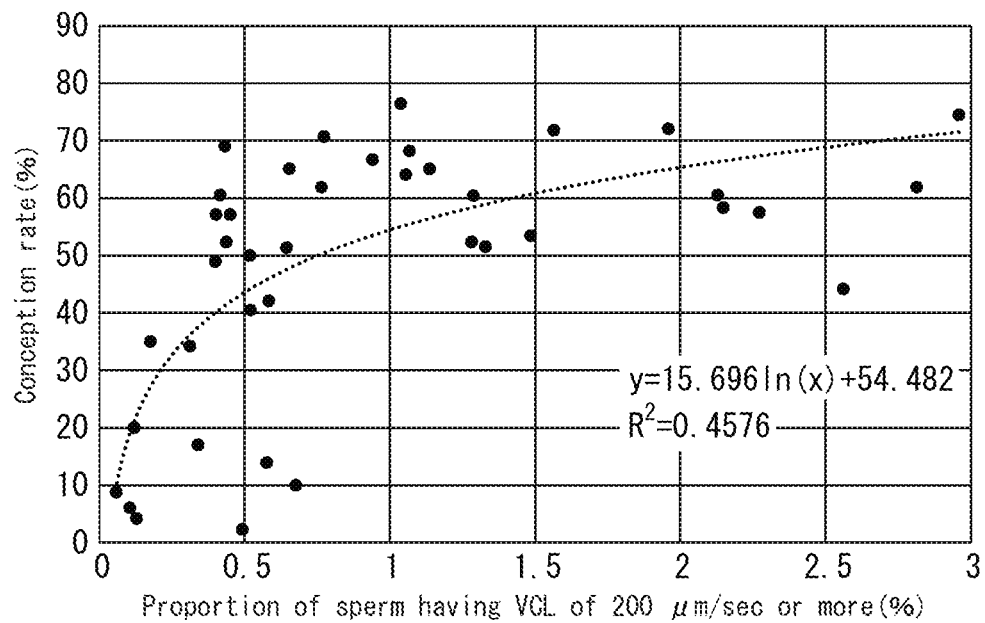
FIG. 7 is a graph showing the correlation between the proportion of sperm having VCL of 200 μm/sec or more and conception rate as a logarithmic approximation determined by measuring 3 lots each of the sperm of 40 bulls having known conception rates. A high correlation (r=0.6765, p<0.001) was able to be confirmed between the proportion of sperm having VCL of 200 μm/sec or more and conception rate.

FIG. 7 shows the results of calculating the correlation between conception rate and the proportion of sperm having VCL of 200 µm/sec or more using logarithmic approximation. The proportion of sperm having VCL of 200 µm/sec or more was able to be confirmed to demonstrate a high correlation with conception rate. It was predicted from this prediction formula that remarkably low fertility is predicted if the proportion of sperm having VCL of 200 µm/sec or more is 0.3% or less, and that conception rate falls below 50% if that proportion is 0.7% or lower. FIGS. 8A and 8B indicate comparisons between the proportion of sperm having VCL of 200 µm/sec or more and conception rate for each category. The proportion of sperm having VCL of 200 µm/sec or more increased as the conception rate of a group became higher.

FIG. 9 shows the results of calculating the correlation between conception rate and the number of sperm having VCL of 200 µm/sec or more per straw using logarithmic approximation. The number of sperm having VCL of 200 µm/sec or more was able to be confirmed to demonstrate a high correlation with conception rate. It was predicted from this prediction formula that remarkably low fertility is predicted if the number of sperm having VCL of 200 µm/sec or more per straw is 100,000 or less, and that conception rate falls below 40% if that number is 300,000 or lower. FIGS. 10A and 10B indicate comparisons between the number of sperm having VCL of 200 µm/sec or more and conception rate for each category (FIG. 10A: n=29, FIG. 10B: n=40). The number of sperm having VCL of 200 µm/sec or more increased as the conception rate of a group became higher.

A histogram of each VCL for all sperm following freezing and thawing for each speed category is shown in FIG. 11 (FIG. 11A: n=29, FIG. 11B: n=40). In the case of low fertility semen, the proportion of sperm having VCL of 200 µm/sec or more was remarkably low, while the proportion of sperm having VCL of 100 to 150 µm/sec was high. The fertility of sperm can be detected with higher reliability by additionally taking into consideration the composition of each VCL in each speed category.

Based on the results shown in FIG. 11B, (1) the proportion was high when conception rate was high in the case of VCL of 150 µm/sec or more. (2) The proportion was higher than bulls having a normal conception rate in the group having a conception rate of less than 40% in the case of VCL of 75 to 150 µm/sec. This indicated that, in the case of bulls having remarkably low fertility, the proportion of sperm having intermediate VCL values is high. (3) In the case of VCL of 25 to 75 µm/sec, the proportion of this sperm was high if conception rate is low. This indicated that, in the case of bulls with low fertility, the proportion of sperm having low VCL is high. (4) The peaks of the VCL histogram were such that bulls having a conception rate of 65% or higher were in the range of 125 to 175 µm/sec, bulls having a conception rate of 55 to 65% were in the range of 50 to 150 µm/sec, and bulls having a conception rate of 40 to 55% were in the range of 50 to 75 µm/sec, with the values of the peaks tending to become higher as conception rate became higher. On the other hand, when bulls having a conception rate of less than 40% were compared with bulls having a conception rate of 40 to 55%, although the proportions of sperm having VCL of 0 to 75 µm/sec were similar, the group having conception rates of less than 40% was characterized by having the highest proportion of sperm having VCL of 75 to 150 µm/sec. In general, the proportion of sperm having high VCL was high when conception rate was high, the proportion of sperm having low VCL was low when conception rate was low, and the proportion of intermediate sperm was high in the case of VCL of bulls having remarkably low fertility. In this manner, sperm populations were indicated as having a characteristic composition for each category of conception rate.

Example 4

Examination of Values Obtained by Arranging VCL Values of all Sperm in Descending Order Frozen semen prepared using ejaculated semen from breeding bulls (n=40) in the Livestock Improvement Association of Japan, Inc. having known conception rates was thawed in accordance with ordinary methods and centrifuged for 5 minutes at room temperature at 2000 rpm for 10 million sperm, followed by removing the supernatant and adding 250 µl of the inspection liquid described in Example 2 to the sediment. The inspection liquid was then incubated for 10 minutes at 38° C. Equal volumes of the inspection liquids to which were added 4% (w/v) polyvinylpyrrolidone K-90 were mixed and then measured using the method described in Example 1. Three lots each were measured for bulls having a conception rate of 65% or more (10 sires), those having a conception rate of 55 to 65% (10 sires), those having a conception rate of 55% or less (10 sires) and those having low fertility (conception rate of less than 40%, 10 sires).

FIG. 12A shows the results of displaying VCL values on the vertical axis and up to the upper 75% of the sperm population on the horizontal axis in descending order. The sperm population was shown to have a characteristic composition for each conception rate division.

FIG. 12B shows the results of displaying VCL values on the vertical axis and up to the upper 75% of the sperm population on the horizontal axis in descending order, and displaying the standard deviations for conception rates of 65% or higher. VCL values for the upper 0.3 to 6% at conception rates of 65% or higher, 55 to 65% and 40 to 55% surpassed the values for low fertility bulls having conception rates of less than 40%. On the basis thereof, conception rate was able to be predicted by comparing arbitrary VCL values of the upper 0.3 to 6%. In addition, fertility was able to be predicted more accurately by comparing with even higher ranking VCL values in the manner of the upper 3%, 2%, 1%, 0.5% or 0.3%.

FIG. 13 displays VCL values on the vertical axis and up to the upper 10% of a sperm population on the horizontal axis in descending order, and indicates the results of calculating approximation lines by approximating with a cubic function. The y intercepts of the cubic function were 216.57, 216.93 and 213.0.4 for normal bulls having conception rates of 65% or more, 55 to 65% and 40 to 55%, respectively, while the y intercept was 200.23 for bulls having a conception rate of less than 40%, with bulls having low fertility exhibiting low values. FIG. 14 displays VCL values on the vertical axis and up to the upper 20% of a sperm population on the horizontal axis in descending order, and indicates the results of calculating approximation lines by linear approximation. The slopes of the lines were −347.4, −395.13 and −421.62 for normal bulls having conception rates of 65% or more, 55 to 65% and 40 to 55%, respectively, while the slope for low fertility bulls having conception rates of less than 40% was −307.04, with samples having remarkably low fertility demonstrating a gentle slope. On the basis thereof, fertility was determined to be able to be predicted more accurately by using the y intercept or slope of an approximation line.

Example 5

Examination of Sperm Fertility Reflective of Composition of a Sperm Population

Frozen semen prepared using ejaculated semen from breeding bulls (n=40) from the Livestock Improvement Association of Japan, Inc. having known conception rates was thawed in accordance with ordinary methods and centrifuged for 5 minutes at room temperature at 2000 rpm for 10 million sperm, followed by removing the supernatant and adding 250 µl of the inspection liquid described in Example 2 to the sediment. The inspection liquid was then incubated for 10 minutes at 38° C. Equal volumes of the inspection liquids to which were added 4% (w/v) polyvinylpyrrolidone K-90 were mixed and then measured using the method described in Example 1. The sperm was evaluated based on the quality indicator values of one or a plurality of groups of the stratified population.

Sperm constituting the upper 72% of VCL values in a sperm population of 1 lot of the frozen semen were divided into 9 groups in 8% increments consisting of the upper 0 to 8%, 8 to 16%, 16 to 24%, 24 to 32%, 32 to 40%, 40 to 48%, 48 to 56%, 56 to 64% and 64 to 72% followed by calculating the VCL values of each group and carrying out multiple regression analysis using 40 bulls having known conception rates. FIG. 15 displays estimated conception rates calculated from an estimation equation obtained from the multiple regression analysis on the vertical axis and actual conception rates on the horizontal axis, and indicates the results of approximation by linear approximation. A high correlation was observed with actual conception rates as a result of evaluating based on the value of a quality indicator in a plurality of groups of the stratified sperm population.

The VCL values of a sperm population of 1 lot of the frozen semen were divided into 5 groups consisting of 0 to 75 µm/sec, 75 to 150 µm/sec, 150 to 175 µm/sec, 175 to 200 µm/sec and 200 µm/sec or more followed by calculating the proportion of sperm in each group and carrying out multiple regression analysis using 40 bulls having known conception rates. FIG. 16 displays estimated conception rates calculated from an estimation equation obtained from the multiple regression analysis on the vertical axis and actual conception rates on the horizontal axis, and indicates the results of approximation by linear approximation. A high correlation was observed with actual conception rates as a result of evaluating based on the value of a quality indicator in a plurality of groups of the stratified sperm population.

Example 6

Comparison Between Fresh Semen and Frozen Semen

Fresh ejaculated semen collected from breeding bulls from the Livestock Improvement Association of Japan, Inc., and frozen semen thawed in accordance with ordinary methods, were centrifuged for 5 minutes at room temperature at 2000 rpm for 10 million sperm, followed by removing the supernatant and adding 250 µl of the inspection liquid described in Example 2 to the sediment. The inspection liquids were then incubated for 10 minutes at 38° C. Equal volumes of the inspection liquids to which were added 4% (w/v) polyvinylpyrrolidone K-90 were mixed and then measured using the method described in Example 1.

The proportions of sperm having VCL of 200 µm/sec or more are shown in FIG. 17. Both fresh sperm and frozen semen were able to be measured, and the proportion of sperm having VCL of 200 μm/sec or more was significantly lower in the frozen semen. On the basis thereof, VCL was able to be confirmed to be able to be used as a sperm quality indicator during the course of technology development such as when developing a diluent for use when preparing frozen semen.

INDUSTRIAL APPLICABILITY

Since the sperm inspection method of the present invention allows the obtaining of an evaluation of sperm that demonstrates a high correlation with conception rate by determining the proportion or number of sperm having an extremely high value for a sperm quality indicator, it can be used to provide high-quality sperm directly from the production site. In addition, since sperm can be provided that reflects fertility, fertility resulting from artificial insemination of cattle in the field can be expected to improve.

The invention claimed is:

1. A sperm inspection device, comprising:
a camera configured to capture an image of a sperm population suspended in an inspection liquid
a processor configured to:
measure a quality indicator value of individual sperm of a sperm population suspended and incubated in an inspection liquid within 1 hour, wherein the quality indicator value is curved line velocity (VCL) and wherein the inspection fluid comprises a loading agent;
stratify the sperm population based on the quality indicator value, and
evaluate sperm quality relating to fertility based on the quality indicator value of a high quality group, wherein the high quality group is within top 10% of the stratified sperm population, wherein the processor determines sperm quality by comparing a quality determination value, which is the mean, median, or mode of a quality indicator value of the high quality group, or the proportion of sperm having a reference value that exceeds or is within a certain range of a reference value of a prescribed quality indicator value of the high quality group, with a reference value of the quality determination value for which a correlation with low fertility samples having conception rates of less than 40% has been indicated in advance.

2. The sperm inspection device according to claim 1, wherein when the quality determination value is the mean, median, or mode of a quality indicator value of the high quality group, the reference value of the quality determination value is curvilinear velocity (VCL) of 175 μm/sec or more.

3. The sperm inspection device according to claim 2, wherein if the quality determination value is lower than 175 μm/sec, then the fertility is determined as lower than 40%.

4. The non-transitory computer-readable medium according to claim 1, wherein when the quality determination value is the proportion of sperm having a reference value that exceeds 175 μm/sec, the reference value of quality determination value is less than 2.5%, then the fertility is determined as lower than 40%.

5. The computer readable medium according to claim 4, when the quality determination value is the mean, median, or mode of a quality indicator value of the high quality group, wherein the reference value of the quality determination value is VCL of 175 μm/sec or more.

6. The computer readable medium according to claim 5, wherein if the quality determination value is lower than 175 μm/sec, then the fertility is determined as lower than 40%.

7. The computer readable medium according to claim 4 or 6, providing a sperm which has fertility not less than 40%.

8. The method according to claim 5, wherein if the quality determination value is lower than 175 μm/sec, then the fertility is determined as lower than 40%.

9. The sperm inspection device according to claim 1, wherein the loading agents is selected from the group consisting of polyvinylpyrrolidone, methyl cellulose, ficoll, polyacrylamide, polyvinyl alcohol, alginic acid, alginic acid salts, hyaluronic acid, hyaluronic acid salts and gelatin.

10. The sperm inspection device according to claim 1, wherein when the quality determination value is the proportion of sperm having a reference value that exceeds 175 μm/sec, the reference value of quality determination value is less than 2.5%, then the fertility is determined as lower than 40%.

11. The sperm inspection device according to claim 1 or 10, providing a sperm which has fertility not less than 40%.

12. The method according to claim 1, wherein when 9 quality determination value is the proportion of sperm having a reference value that exceeds 175 μm/sec, the reference value of quality determination value is less than 2.5%, then the fertility is determined as lower than 40%.

13. The method according to claim 8 or 12, providing a sperm which has fertility not less than 40%.

14. A non-transitory computer-readable medium storing a computer program, wherein the computer program causes a sperm inspection device which comprises a camera and a processor to execute following processes:
capturing an image of a sperm population suspended in an inspection liquid,
measuring a quality indicator value of individual sperm of a sperm population suspended in an inspection liquid based on the image, wherein the quality indicator value is curved line velocity (VCL);
stratifying the sperm population based on the quality indicator, and
evaluating sperm quality based on the quality indicator value of a high quality group, wherein the high quality group is within the top 10% of the stratified sperm population, wherein sperm quality is determined by comparing a quality determination value, which is the mean, median, or mode of a quality indicator value of the high quality group, or the proportion of sperm having a reference value that exceeds or is within a certain range of a reference value of a prescribed quality indicator value of the high quality group, with a reference value of the quality determination value for which a correlation with low fertility samples having conception rates of less than 40% has been indicated in advance.

15. A method for controlling a sperm inspection device, comprising a camera and a processor, comprising:
operating the high speed camera to capture an image of a sperm population suspended in an inspection liquid,
operating the processor to measure a quality indicator value of individual sperm of a sperm population suspended in an inspection liquid, based on the image, wherein the quality indicator value is curved line velocity (VCL);
stratifying the sperm population based on the quality indicator value, and
evaluating sperm quality based on the quality indicator value of a high quality group, wherein the high quality group is within the top 10% of the stratified sperm population, wherein sperm quality is determined by comparing a quality determination value, which is the mean, median, or mode of a quality indicator value of the high quality group, or the proportion of sperm having a reference value that exceeds or is within a certain range of a reference value of a prescribed quality indicator value of the high quality group, with a reference value of the quality determination value for which a correlation with low fertility samples having conception rates of less than 40% has been indicated in advance.

16. The method according to claim 15, wherein the reference value of quality indicator is VCL of 175 μm/sec or more.

* * * * *